US012256949B2

(12) United States Patent
Dacosta et al.

(10) Patent No.: US 12,256,949 B2
(45) Date of Patent: Mar. 25, 2025

(54) INTRAMEDULLARY NAIL FIXATION GUIDES, DEVICES, AND METHODS OF USE

(71) Applicant: Paragon 28, Inc., Englewood, CO (US)

(72) Inventors: Albert Dacosta, Lone Tree, CO (US); Frank Bono, Castle Rock, CO (US); Michael Houghton, Fort Collins, CO (US); Thomas Sangiovanni, Miami, FL (US); James T. Clancy, Atlantis, FL (US); Thomas Chang, Santa Rosa, CA (US)

(73) Assignee: Paragon 28, Inc., Englewood, CO (US)

( * ) Notice: Subject to any disclaimer, the term of this patent is extended or adjusted under 35 U.S.C. 154(b) by 587 days.

(21) Appl. No.: 17/456,191

(22) Filed: Nov. 23, 2021

(65) Prior Publication Data

US 2022/0079607 A1  Mar. 17, 2022

Related U.S. Application Data

(63) Continuation of application No. 15/911,680, filed on Mar. 5, 2018, now Pat. No. 11,179,166, which is a
(Continued)

(51) Int. Cl.
*A61B 17/17* (2006.01)
*A61B 17/56* (2006.01)
(Continued)

(52) U.S. Cl.
CPC ...... *A61B 17/1717* (2013.01); *A61B 17/1725* (2013.01); *A61B 17/72* (2013.01);
(Continued)

(58) Field of Classification Search
CPC .......................... A61B 17/72; A61B 17/1725
(Continued)

(56) References Cited

U.S. PATENT DOCUMENTS 4,522,202 A   6/1985  Otte
4,875,475 A   10/1989 Comte
(Continued)

FOREIGN PATENT DOCUMENTS

CA   2845255      2/2013
WO   2011072249   6/2011
WO   2012033836   3/2012

OTHER PUBLICATIONS

International Search Report and Written Opinion of the International Searching Authority for PCT/US2014/027086, Sep. 10, 2014, 10 pages.

*Primary Examiner* — Eduardo C Robert
*Assistant Examiner* — Tara Rose E Carter
(74) *Attorney, Agent, or Firm* — Heslin Rothenberg Farley & Mesiti P.C.; Jacquelyn A. Graff, Esq.

(57) ABSTRACT

Fixation guide devices and methods for positioning and inserting an intramedullary nail are disclosed. The fixation guide devices include a frame with a first end and a second end, a compression device removably coupled to the first end of the frame, and the intramedullary nail secured to a nail attachment apparatus of the frame. An intramedullary nail including a body with a fastening end, a closed end, and at least two openings is also disclosed. A compression device includes a compression member, a knob, and a bolt secured in the knob and rotatably engaging the compression member is also disclosed. An alignment guide is disclosed and includes a base member, an alignment member, and a fixation guide. A method of inserting an intramedullary nail into two bones for fixation of the two bones is also disclosed.

18 Claims, 26 Drawing Sheets

Related U.S. Application Data continuation of application No. 14/776,418, filed as application No. PCT/US2014/027086 on Mar. 14, 2014, now Pat. No. 9,907,562.

(60) Provisional application No. 61/793,212, filed on Mar. 15, 2013.

(51) Int. Cl.
  *A61B 17/68* (2006.01)
  *A61B 17/72* (2006.01)

(52) U.S. Cl.
  CPC ... *A61B 2017/564* (2013.01); *A61B 2017/681* (2013.01); *A61B 17/7291* (2013.01)

(58) Field of Classification Search
  USPC .................................................. 606/62–68
  See application file for complete search history.

(56) References Cited

U.S. PATENT DOCUMENTS

| | | |
|---|---|---|
| 5,066,296 A | 11/1991 | Chapman |
| 5,352,228 A | 10/1994 | Kummer |
| 5,766,174 A * | 6/1998 | Perry ................. A61B 17/1725 606/62 |
| 6,235,031 B1 | 5/2001 | Hodgeman |
| 6,629,976 B1 | 10/2003 | Gnos |
| 8,398,690 B2 | 3/2013 | Bottlang |
| 2004/0215204 A1 | 10/2004 | Davison |
| 2005/0277936 A1 | 12/2005 | Siravo |
| 2006/0100623 A1 | 5/2006 | Pennig |
| 2007/0123873 A1 | 5/2007 | Czartoski |
| 2007/0123876 A1* | 5/2007 | Czartoski ............. A61B 17/744 606/62 |
| 2007/0255283 A1 | 11/2007 | Ekholm |
| 2009/0048598 A1 | 2/2009 | Ritchey |
| 2009/0157077 A1 | 6/2009 | Larsen |
| 2009/0248024 A1 | 10/2009 | Edwards |
| 2011/0009865 A1 | 1/2011 | Orfaly |
| 2011/0054475 A1 | 3/2011 | Metzinger |
| 2011/0282346 A1 | 11/2011 | Pham |
| 2012/0197254 A1 | 8/2012 | Wolfe |
| 2012/0209268 A1 | 8/2012 | Overes |
| 2012/0215222 A1 | 8/2012 | Yapp |
| 2012/0221005 A1 | 8/2012 | Corneille |
| 2012/0259333 A1 | 10/2012 | Ritchey |
| 2013/0110119 A1 | 5/2013 | Atkinson |

* cited by examiner

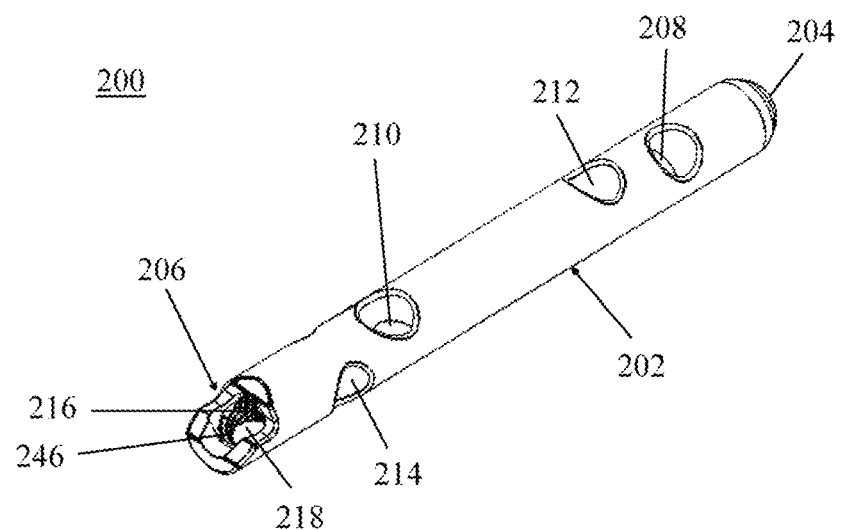
FIG. 9
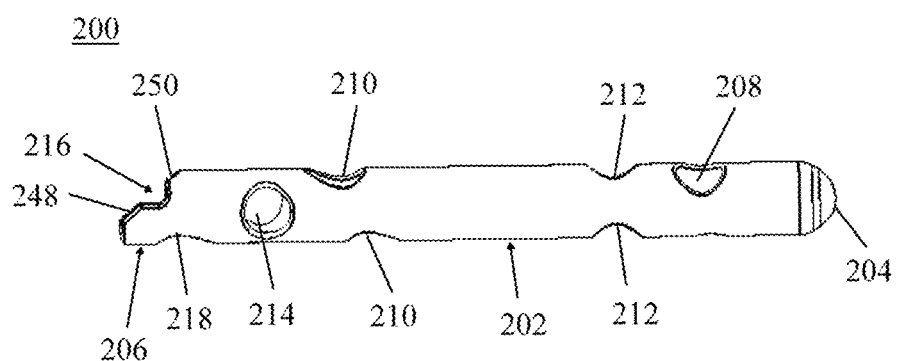
FIG. 10
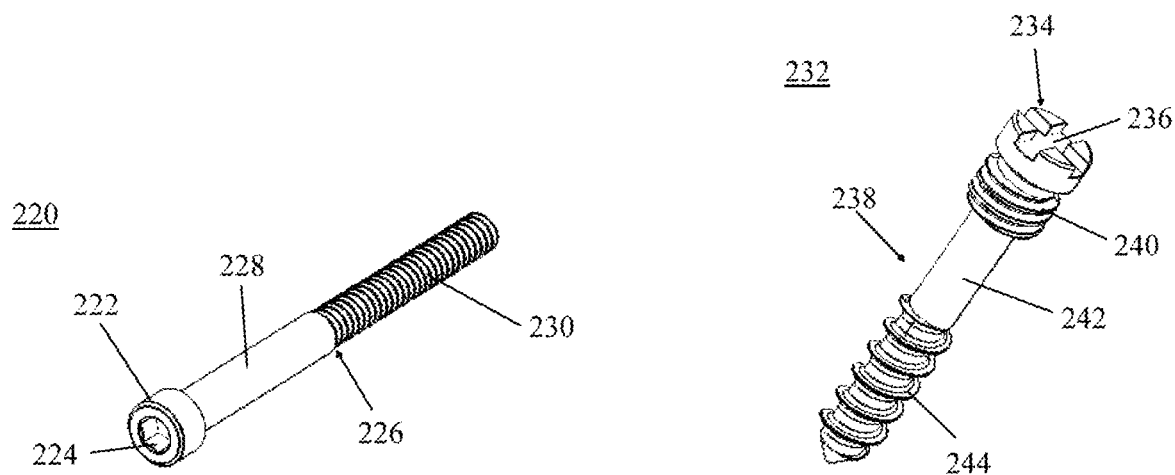
FIG. 11
FIG. 12

INTRAMEDULLARY NAIL FIXATION GUIDES, DEVICES, AND METHODS OF USE

CROSS REFERENCE TO RELATED APPLICATIONS

This application is a continuation of U.S. application Ser. No. 15/911,680 filed Mar. 5, 2018, entitled Intramedullary Nail Fixation Guides, Devices, and Methods of Use, which issues as U.S. Pat. No. 11,179,166 on Nov. 23, 2021; which is a continuation of U.S. application Ser. No. 14/776,418 filed Sep. 14, 2015, which issued as U.S. Pat. No. 9,907,562 on Mar. 6, 2018, entitled Intramedullary Nail Fixation Guides, Devices, and Methods of Use; which is a national stage filing under section 371 of International Application No. PCT/US2014/027086 filed Mar. 14, 2014, and published in English on Sep. 25, 2014 as WO 2014/152219, entitled Intramedullary Nail Fixation Guides, Devices, and Methods of Use; which claims priority benefit under 35 U.S.C. § 119(e) of U.S. provisional application No. 61/793,212 filed Mar. 15, 2013, entitled Intramedullary Nail Fixation Guides, Devices, and Methods of Use, which are incorporated herein by reference in their entireties.

TECHNICAL FIELD

The present disclosure relates generally to the field of orthopedics related to fixation of prepared joint surfaces using intramedullary nail fixation guides, devices, and methods.

BACKGROUND OF THE INVENTION

The current technology utilizes plate and screw fixation that needs a balance between strength and plate profile. The soft tissue coverage of the joints in question is not sufficient to prevent irritation from thick plates and screw heads. In addition, the attachment of tendons and other anatomical considerations cause most plating to occur at the dorsal surface of the joint which is the "compression side" and very little can be done to prevent "gapping" at the plantar surface which is the "tension side." Therefore, plating needs to be very thin to prevent soft tissue irritation and the need for a second operation to remove the plating. As the position of implantation is on the compression side weight bearing must be postponed for six to eight weeks to prevent hardware and fusion failure. Prolonged periods of non-weight bearing create increased probability of compromised healing.

Accordingly, the present invention contemplates new and improved intramedullary nail fixation guides, devices, and methods which overcome the above-referenced problems and others.

SUMMARY OF THE INVENTION

The present invention is directed toward devices and methods for use in fixation of a patient's joints or for fixation of a fracture. The fixation guides provide an orientation for insertion of intramedullary nails through a patient's joint or fracture to maximize the strength of the joint and bones based on the length of the nail and to minimize weakening of the bone for better plantar stabilization.

In one aspect of the present invention provided herein, is a fixation guide device for positioning and inserting an intramedullary nail. The fixation guide device includes a frame with a first end and a second end. The fixation guide device also includes a compression device removably coupled to the first end of the frame. In addition, the fixation guide device includes the intramedullary nail secured to a nail attachment apparatus of the frame.

In another aspect of the present invention provided herein, is an intramedullary nail including a body with a first end and a second end. The body includes a fastening end at the first end, a closed end at the second end, and at least two openings positioned oblique to the longitudinal axis of the body between the first end and the second end of the body. The fastening end includes an insertion opening extending from the first end into the body along a longitudinal axis of the body.

In another aspect of the present invention provided herein, is a compression device for compressing a joint with an implant. The compression device includes a compression member, a knob, and a bolt secured in the knob and rotatably engaging the compression member.

In yet another aspect of the present invention provided herein, is an alignment guide including a base member, an alignment member, and a fixation guide. The base member includes a first portion and a second portion with the second portion extending out from the first portion in a relatively perpendicular direction and the first portion including at least one opening. The alignment member including at least one opening, being coupled to the base member, and angled relative to the second portion of the base member. The fixation guide removably inserted through one of the at least one openings in the first portion of the base member.

In a further aspect of the present invention provided herein, is a method of inserting an intramedullary nail into two bones for fixation of the two bones. The method may include creating an incision near the two bones and preparing the two bones for fixation. The method may further include securing an alignment guide to the two bones to position a guidewire across the two bones. Next, the method may include drilling over the guidewire to create a cavity for the intramedullary nail to pass through the two bones. The intramedullary nail includes a securing screw hole at a first end of the intramedullary nail and at least two peg holes. The method may also include obtaining a fixation guide device. The fixation guide device includes a frame with at least two drill holes and a compression device. The method may further include attaching the intramedullary nail to the compression device of the fixation guide device and inserting the intramedullary nail into the cavity. The method may also include inserting a drill sleeve into a first drill hole at a second end of the fixation guide device and drilling a first opening that aligns with a first peg hole in the second end of the intramedullary nail. Next, the method may include inserting a first peg into the first opening and through the first peg hole. The method may then include using the first peg and compression device to compress the two bones. The method may further include inserting the drill sleeve into a second drill hole at the first end of the fixation guide device and drilling a second opening that mates with a second peg hole in the first end of the intramedullary nail. The method may also include inserting a second peg into the second opening and through the second peg hole to secure the two bones in compression. Further, the method may include detaching the intramedullary nail from the fixation guide and removing the fixation guide device. The method may also include inserting a locking screw into the securing screw hole. Finally, the method may include closing the incision.

These and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

FIG. 9 is an isometric view of an intramedullary nail of the fixation guide of FIG. 1, in accordance with an aspect of the present invention;

FIG. 10 is a side view of the intramedullary nail of FIG. 9, in accordance with an aspect of the present invention;

FIG. 11 shows an isometric view of an intramedullary nail engagement fastener of the fixation guide of FIG. 1, in accordance with an aspect of the present invention;

FIG. 12 is an isometric view of an intramedullary nail locking screw of the fixation guide of FIG. 1, in accordance with an aspect of the present invention;

DETAILED DESCRIPTION FOR CARRYING OUT THE INVENTION

In this application, the words proximal, distal, anterior or plantar, posterior or dorsal, medial and lateral are defined by their standard usage for indicating a particular part or portion of a bone or prosthesis coupled thereto, or directional terms of reference, according to the relative disposition of the natural bone. For example, "proximal" means the portion of a bone or prosthesis nearest the torso, while "distal" indicates the portion of the bone or prosthesis farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, instrumentation and methods are described herein with reference to use with the bones of the foot, the bones of the foot, ankle and lower leg may be used to describe the surfaces, positions, directions or orientations of the devices, instrumentation and methods. Further, the devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices, instrumentation and methods, and the aspects, components, features and the like thereof, described herein with respect to the right foot may be mirrored so that they likewise function with the left foot. Further, the devices, instrumentation and methods, and the aspects, components, features and the like thereof, disclosed herein are described with respect to the foot for brevity purposes, but it should be understood that the devices, instrumentation, and methods may be used with other bones of the body having similar structures, for example the upper extremity, and more specifically, with the bones of the wrist, hand, and arm.

Figure 1:
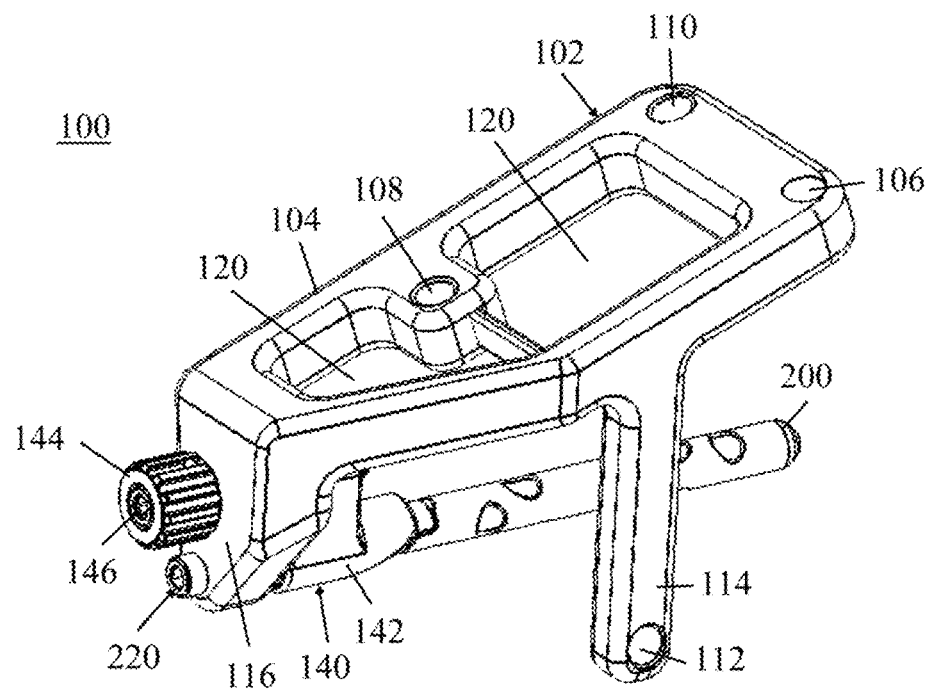
FIG. 1 shows an isometric view from the lateral side of one embodiment of an implant fixation guide, in accordance with an aspect of the present invention.
Figure 2:
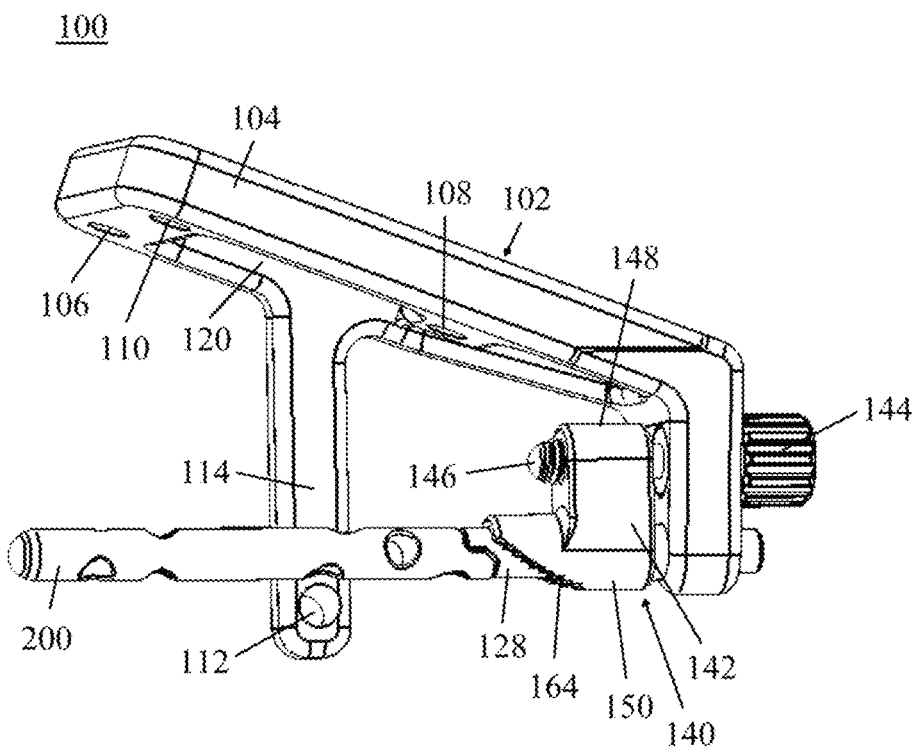
FIG. 2 shows an isometric view from the medial side of the fixation guide of FIG. 1, in accordance with an aspect of the present invention.
Figure 3:
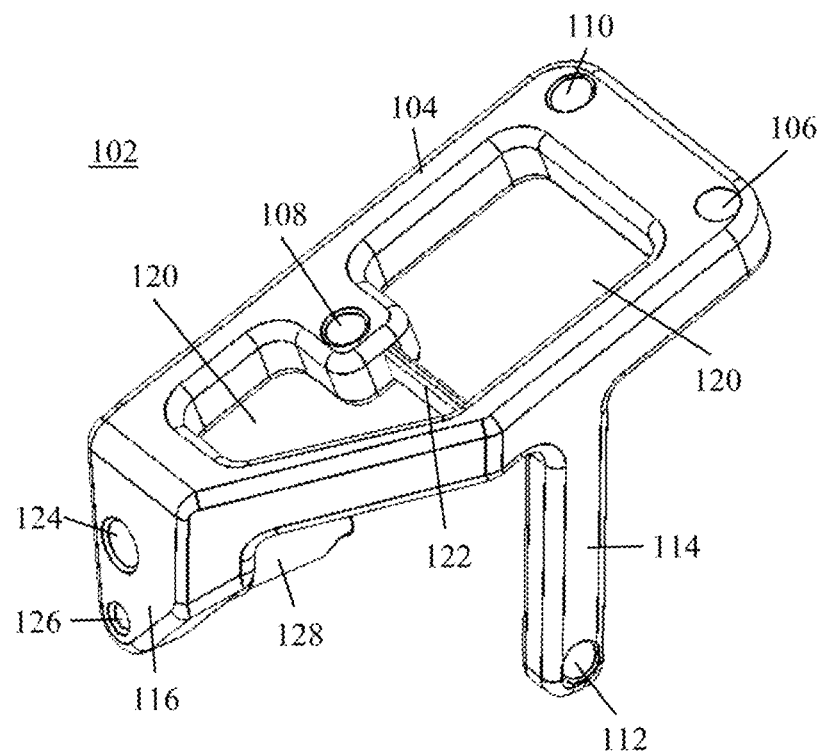
FIG. 3 shows an isometric view from the lateral side of an outrigger assembly of the fixation guide of FIG. 1, in accordance with an aspect of the present invention.
Figure 4:
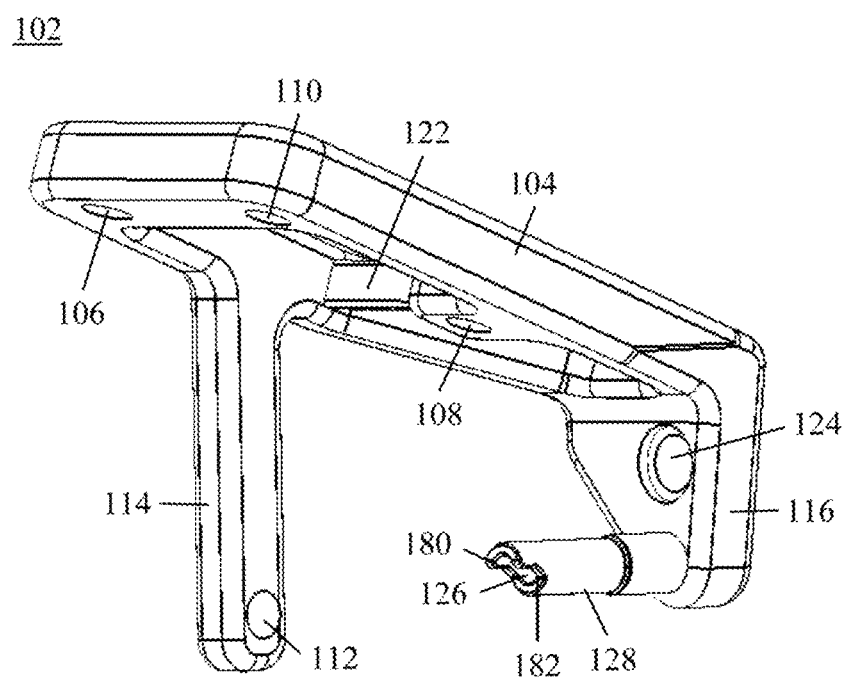
FIG. 4 is an isometric view from the medial side of the outrigger assembly of FIG. 3, in accordance with an aspect of the present invention.

Referring to the drawings, wherein like reference numerals are used to indicate like or analogous components throughout the several views, and with particular reference to FIGS. 1-2, there is illustrated an exemplary embodiment fixation guide device 100. The fixation guide device 100 includes an outrigger assembly or frame 102 which may be coupled to a compression device 140 and an intramedullary nail 200. In the embodiment depicted in FIGS. 3-4, the outrigger assembly 102 includes a base 104 with a first drill hole 106, a second drill hole 108, a third drill hole 110, a second or lateral arm 114 with a fourth drill hole 112, and a first or distal arm 116. It is also contemplated that the frame 102 may include, for example, a plurality of drill holes 106, 108, 110, 112 as necessary to secure the intramedullary nail 200 across a joint or fracture. The drill holes 106, 108, 110, 112 may each include, for example, multiple holes spaced a small distance apart or multiple nested or overlapping holes to correspond to the openings 208, 210, 212, 214 in multiple size intramedullary nails 200. The frame 102 may include a first end and a second end. The base 104 may include at least one opening 120 allowing for visualization through the base 104 with imaging technology, such as x-rays, and a bracket 122, as seen in FIG. 3, for stabilization of the fixation guide device 100 where the opening 120 is large. The bracket 122 may provide stability to the base 104 allowing for alignment of the fasteners for insertion in the nail 200. The distal arm 116 is perpendicular to the base 104 at the distal end and includes a knob opening or first opening 124, a nail attachment opening or second opening 126, and a nail attachment portion or apparatus 128. The nail attachment portion 128 includes an end with an inverted two step profile including a first step or first nail attachment segment 180 extending a first distance and a second step or second nail attachment segment 182 extending a second distance. The first distance is greater than the second distance. The base 104 is ideally made of a material that is strong enough to prevent deformation during surgery, such as a metal, while also being radiolucent to allow for imaging through the base 104 to determine if correct alignment of the nail 200 was achieved. The base 104 may be made of, for example, carbon fiber.

Figure 5:
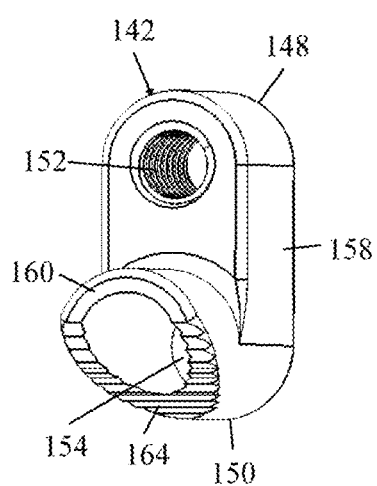
FIG. 5 is a front isometric view of a compression member of the fixation guide of FIG. 1, in accordance with an aspect of the present invention.
Figure 6:
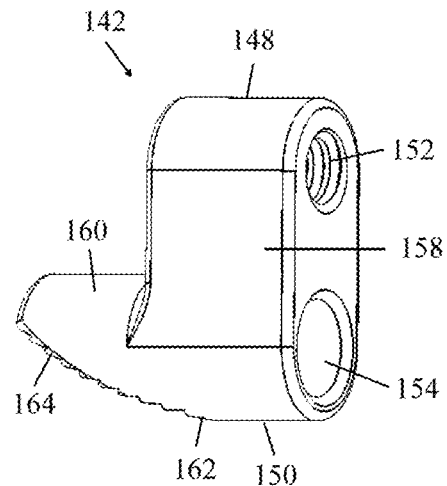
FIG. 6 is a side isometric view of the compression member of FIG. 5, in accordance with an aspect of the present invention.

The compression device 140 slidingly mates with the nail attachment portion 128. The compression device 140 includes a compression member 142, a knob 144, and a bolt 146. As best seen in FIGS. 5-6, the compression member 142 has a base 158 with a top end 148 and a bottom end 150. The compression member 142 also includes a protrusion 160 at the bottom end 150. A first opening 152 is near the top end 148 for receiving bolt 146. The first opening 152 is threaded to mate with a threaded end 156 of bolt 146. A second opening 154 is near the bottom end 150 and passes through the base 158 and protrusion 160. The second opening 154 is slidingly engaged with the nail attachment portion 128. The proximal end of the compression member 142 is angled from a point between the top and midline of the protrusion 160 to approximately a midpoint 162 of the bottom end 150 of the base 158 of the compression member 142. The angled portion of the protrusion 160 may include teeth 164 for engaging a patient's bone.

Figure 7:
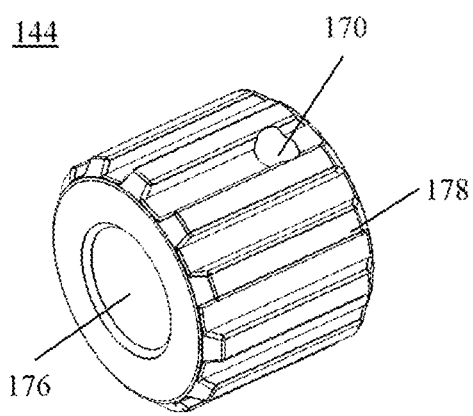
FIG. 7 shows a front isometric view of a compression device knob of the fixation guide of FIG. 1, in accordance with an aspect of the present invention.
Figure 8:
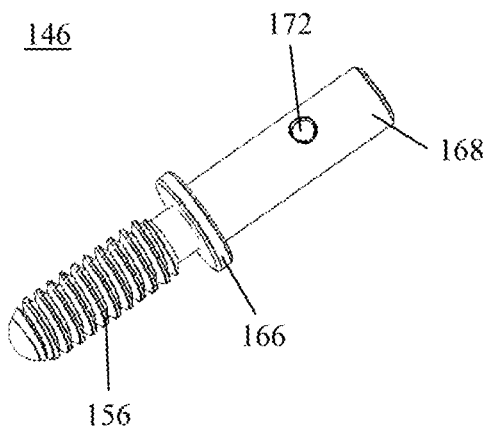
FIG. 8 is a side isometric view of a compression device bolt of the fixation guide of FIG. 1, in accordance with an aspect of the present invention.

As depicted, after the compression member 142 is slid over nail attachment portion 128, the knob 144 may be secured to the base 104 using a bolt 146 and a fastener (not shown). The knob 144 is shown in FIG. 7 and bolt 146 is illustrated in FIG. 8. The threaded end 156 of bolt 146 is inserted into knob opening 124 and the threaded end 156 mates with the threads of the second opening 154. The bolt 146 also includes a stop member 166 and a smooth end 168. The stop member 166 prevents bolt 146 from passing through knob opening 124. The smooth end 168 of bolt 146 may be inserted into an opening 176 in the knob 144. The bolt 146 and knob 144 are locked in place with a fastener (not shown), such as a pin, clip, or the like, inserted through opening 170 of the knob 144 and bolt opening or opening 172. Opening 170 is generally perpendicular to opening 176 and passes through the entire knob 144. The knob 144 may also include ridges 178 on an exterior surface to aide in the rotation of the knob 144 by the surgeon.

Referring now to FIGS. 9-10 with continued reference to FIGS. 1-2, the intramedullary nail 200 includes a body 202 with a closed end 204, a fastening end 206, and four openings 208, 210, 212, 214. The four openings 208, 210, 212, 214 may be disposed on independent planes and angularly spaced apart relative to each other. By placing the four openings 208, 210, 212, 214 at opposing angles oblique to the longitudinal axis of the nail 200, the amount of longitudinal and rotational movement of the nail 200 is limited. It is also contemplated that the intramedullary nail 200 may include any number of openings 208, 210, 212, 214 as may be necessary to secure the nail to a patient's bones. The fastening end 206 includes an insertion opening 216 and an engagement opening 218. The insertion opening 216 is a threaded opening along a longitudinal axis in the center of the nail 200 parallel to the exterior surface of the nail 200. The insertion opening 216 is used to secure the nail 200 to the nail attachment portion 128 using an engagement fastener 220, such as a screw. The engagement opening 218 may include a central axis that is generally transverse the longitudinal axis of the nail 200. As illustrated in FIG. 11, the engagement fastener 220 includes a head 222 with a drive opening 224 and a shank 226 that is partially threaded including a smooth portion 228 and a threaded portion 230. The drive opening 224 may be, for example, hexagonal, square, Phillips or another multi-lobed configuration for coupling with an insertion instrument. The engagement fastener 220 is inserted through opening 126 and passes through the nail attachment portion 128 before being screwed into the insertion opening 216 to secure nail 200 to the nail attachment portion 128.

The engagement opening 218 of the nail 200 may be a threaded opening that passes through the exterior surface of nail 200 to secure the nail 200 to the bone using a fastener, such as a locking screw 232. The locking screw 232 is depicted in FIG. 12 and includes a head 234 with a drive opening 236 and a shank 238 with a first threaded section 240, a smooth section 242, and a second threaded section 244. The drive opening 236 may be, for example, a Phillips opening, a flat head opening, a hexagonal opening, or other multi-lobed configuration. The second threaded section 244 is designed to engage the patient's bone. The first threaded section 240 of the locking screw 232 is threaded to correspond to the threads 246 of the engagement opening 218 to secure the nail 200 in place inside the patient's bones. The first threaded section 240 may have a larger diameter than the second threaded section 244 allowing for the second threaded section 244 to pass through the opening 218 without engaging the threads 246. Alternatively, the first threaded section 240 and second threaded section 244 may have the same diameters such that the second threaded section 244 would mate with the threads 246 as it passes through the opening 218. For example, the threads of the first threaded section 240 and second threaded section 244 may have the same pitch to allow both the first threaded section 240 and second threaded section 244 to mate with opening 218. In order to provide for thread differentiation between the first threaded section 240 and second threaded section 244 the second threaded section 244 may have a single lead thread and the first threaded section 240 may include a double lead thread in order to improve bone purchase.

The nail 200 may also include a fastening end 206 with a shape that corresponds to the shape of the end of the nail attachment portion 128 to create a tight fit between the nail 200 and the attachment portion 128. As depicted in FIGS. 9-10, the fastening end 206 may have a two step profile including a first step or first fastening segment 248 and a second step or second fastening segment 250. When the nail 200 is secured to the outrigger assembly 102 the first fastening segment 248 aligns with second nail attachment segment 182 and second fastening segment 250 aligns with first nail attachment segment 180. The engagement fastener 220 may then be inserted to secure the nail 200 to the outrigger assembly 102. The step profiles of the nail 200 and the nail attachment portion 128 provide additional stability to the nail 200 during insertion into the patient's bone and prevent nail 200 from rotating during insertion of the pegs and screws.

Figure 55:
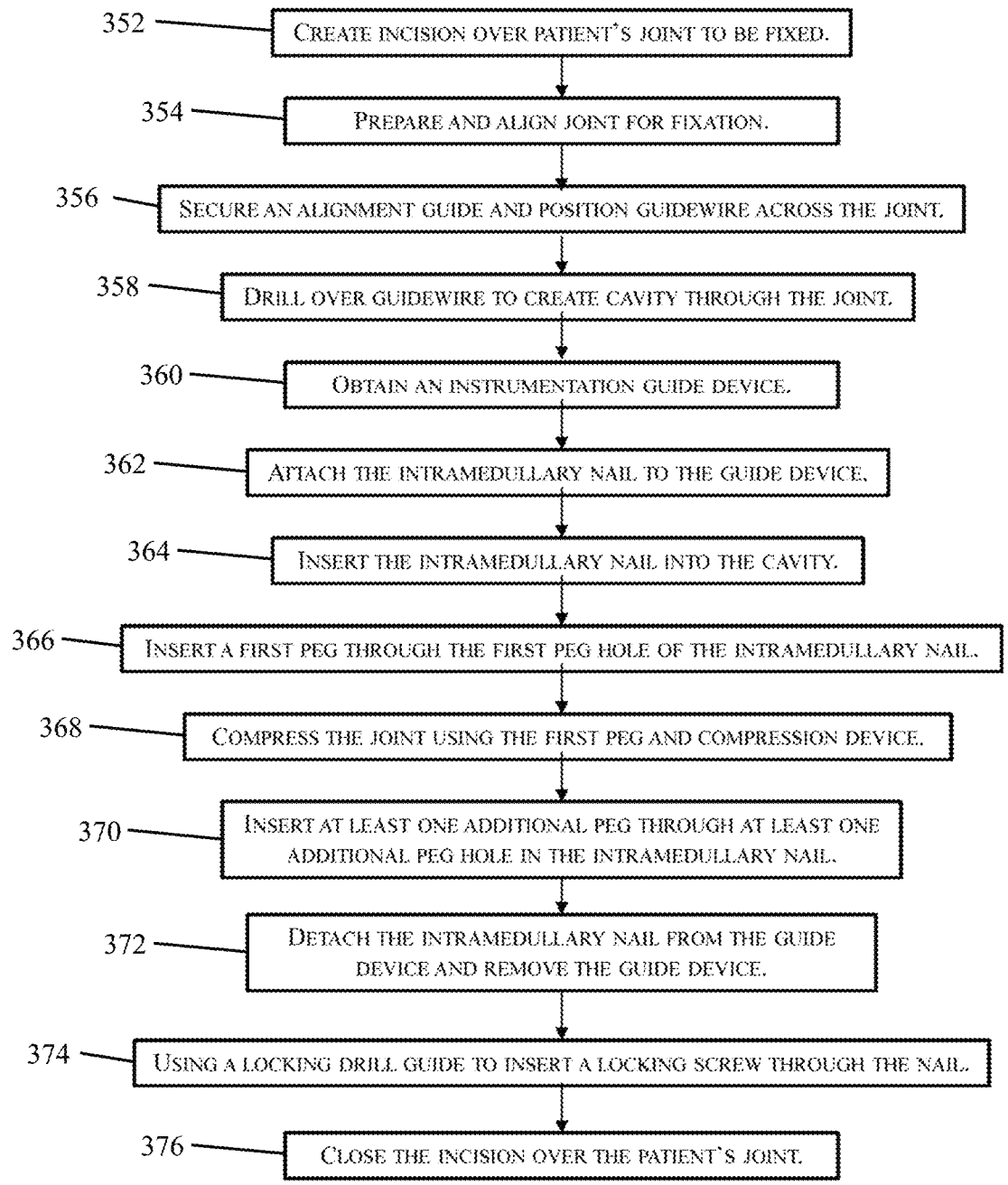
FIG. 55 depicts one embodiment of a method of inserting an intramedullary nail into a joint for fixation of the joint, in accordance with an aspect of the present invention.
Figure 56:
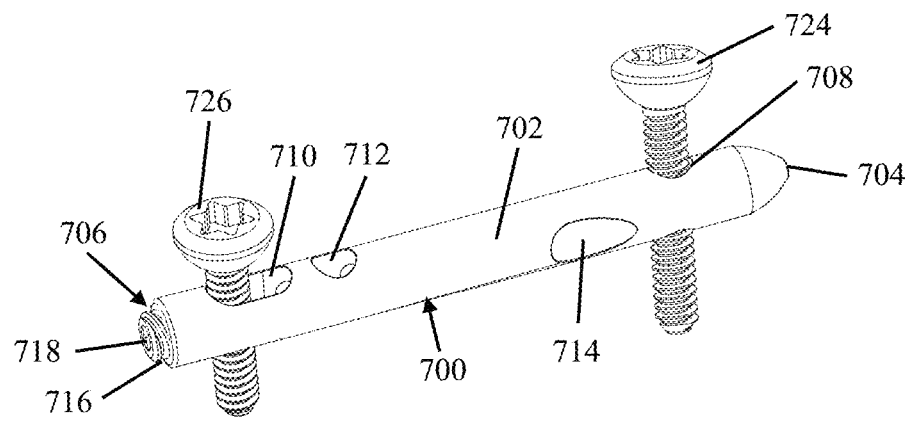
FIG. 56 is an isometric view of another intramedullary nail implant with two fasteners inserted, in accordance with an aspect of the present invention.

The surgical method for inserting the intramedullary nail 200 into a patient's joint 260 may include the steps of FIG. 55, as illustrated in FIGS. 13-32. The method utilizes some of the devices, instruments, features, aspects, components, and the like described above, and therefore reference will be made to the above described embodiments, such as the illustrated embodiments presented in the figures and discussed above. However, such references are made for exemplary purposes only and are not intended to limit the surgical method beyond the specifically recited steps. Further, the surgical method may be discussed under the umbrella of particular bones, but such an application is not intended to be limiting and the method described herein may be used or conducted with bone or other tissue not specifically discussed herein without departing from the spirit and scope of the surgical method.

If a joint 260, for example, a proximal tarsal-metatarsal joint or the like, needs to be surgically fixed, a surgeon would first expose the joint 260 by creating an incision over the joint 260 shown in step 352. Next, in step 354, the first bone 262 and second bone 264 of the joint 260 will be prepared by using a cut guide and cartilage removal technique such as curet, osteotome, saw blade, or other similar cartilage removal technique known by one skilled in the art. The joint 260 is then aligned by moving the first bone 262 and second bone 264 into a desired position for fixation. Once the bones 262, 264 are aligned, temporary fixation may be applied to hold the joint 260 in the desired position. A guidewire, template, or similar clamp may be used to temporarily fix the joint 260.

Figure 13:
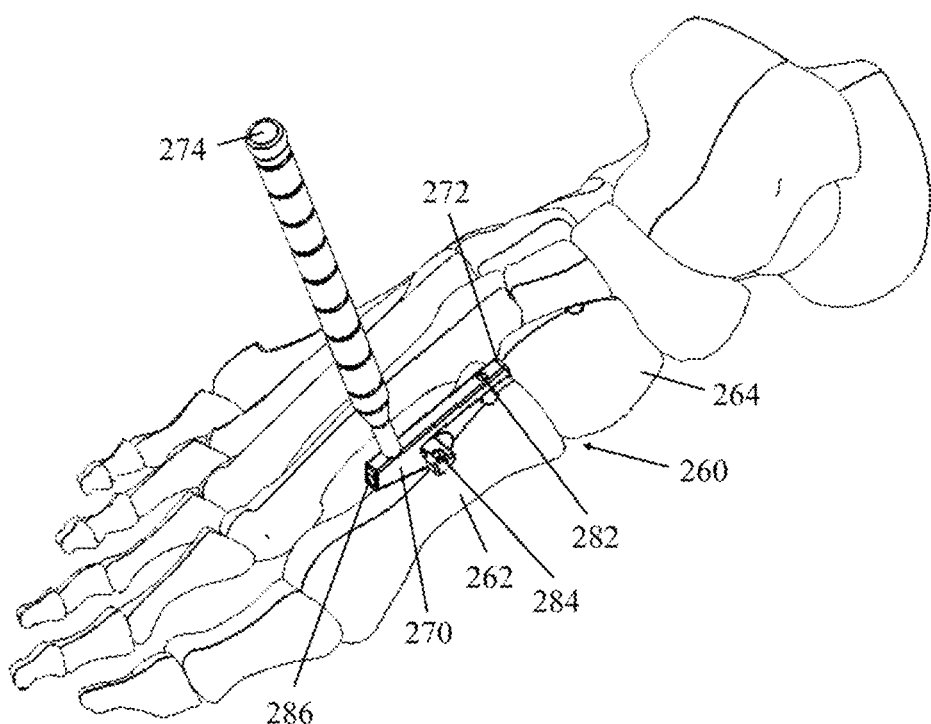
FIG. 13 is an isometric view of a guidewire alignment guide mounted onto a foot of a patient, in accordance with an aspect of the present invention.
Figure 14:
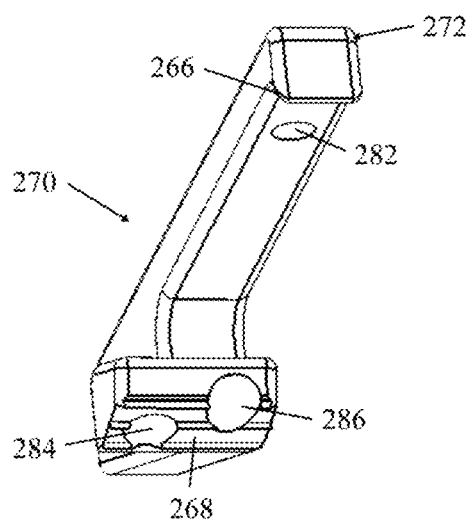
FIG. 14 is a rear isometric view of the guidewire alignment guide of FIG. 13, in accordance with an aspect of the present invention.

Next, in step 356, as seen in FIG. 13, a guidewire alignment guide 270 is positioned onto the first bone 262 with the first end 272 of the alignment guide 270 aligned with the proximal end, for example, the dorsal ridge, of the first bone 262 at the joint 260 to align the guide 270. The alignment guide 270, shown in FIG. 14, may include a first opening 282 on the proximal end of the guide 270, a second opening 284 on the lateral side of the guide 270, and a third opening 286 on the front of the distal end of the guide 270. As seen in FIG. 14, the guidewire alignment guide 270 may also include a rim 266 at the first end 272 that mates with the edge of the first bone 262 to hold the alignment guide 270 in place. In addition, the alignment guide 270 may include teeth 268 for mating with the first bone 262 to maintain a desired position while inserting the guidewires 276. A handle 274 may add additional stability to hold the alignment guide 270 in position while guidewires 276, 278, 280 are inserted into the bone. The guidewires 276, 278, 280 may be, for example, K-wires.

Figure 15:
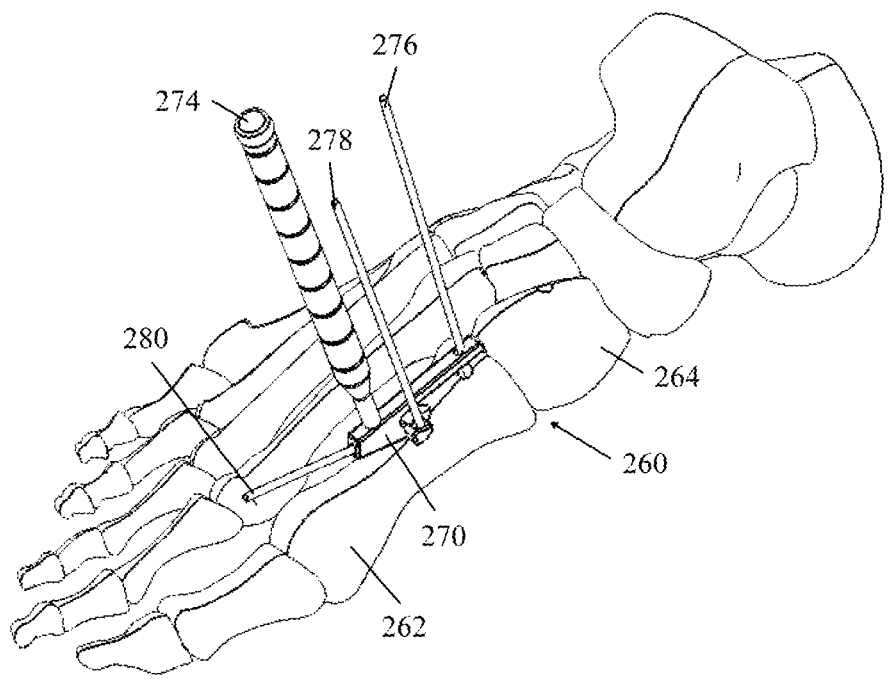
FIG. 15 is an isometric view showing the guidewire alignment guide of FIG. 14 mounted onto the foot of the patient with three guidewires inserted into the patient's bone, in accordance with an aspect of the present invention.
Figure 16:
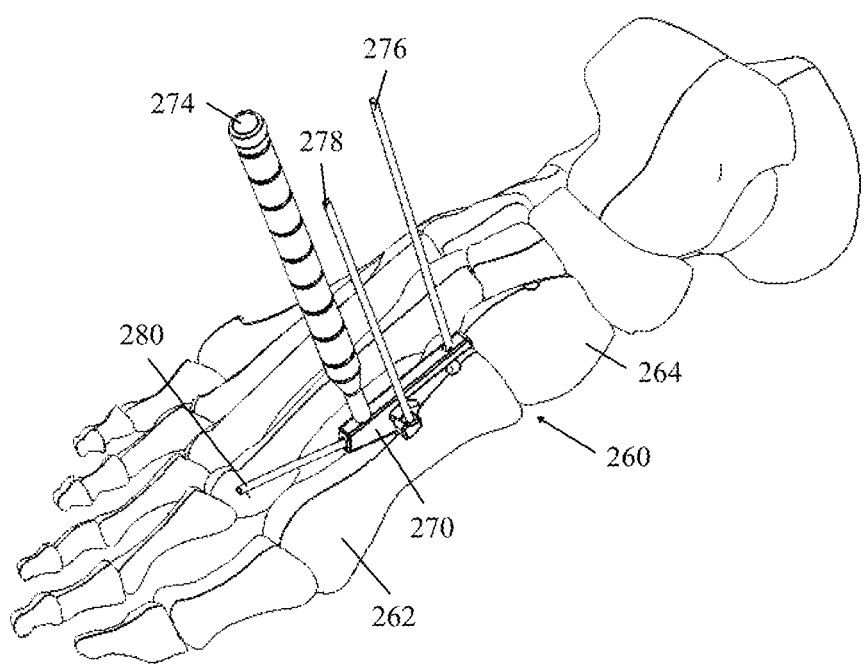
FIG. 16 is an isometric view of one of the three guidewires inserted into the patient's foot across a joint, in accordance with an aspect of the present invention.

Referring now to FIG. 15, the first guidewire 276 may then be inserted through first opening 282 and into the proximal end of the first bone 262. The guide 270 may be rotated about the first guidewire 276 if necessary for proper alignment. The second guidewire 278 may be inserted through second opening 284 and into the medial side of the first bone 262. The third guidewire 280 may be inserted through the third opening 286 and across the joint 260. The third guidewire 280 may be positioned to be used as a drilling guide for the intramedullary nail 200. Once the third guidewire 280 is inserted across the joint 260 the first guidewire 276, second guidewire 278, and guidewire alignment guide 270 may be removed, leaving the third guidewire 280 in position for drilling a cavity for the nail 200, as illustrated in FIG. 16.

Figure 17:
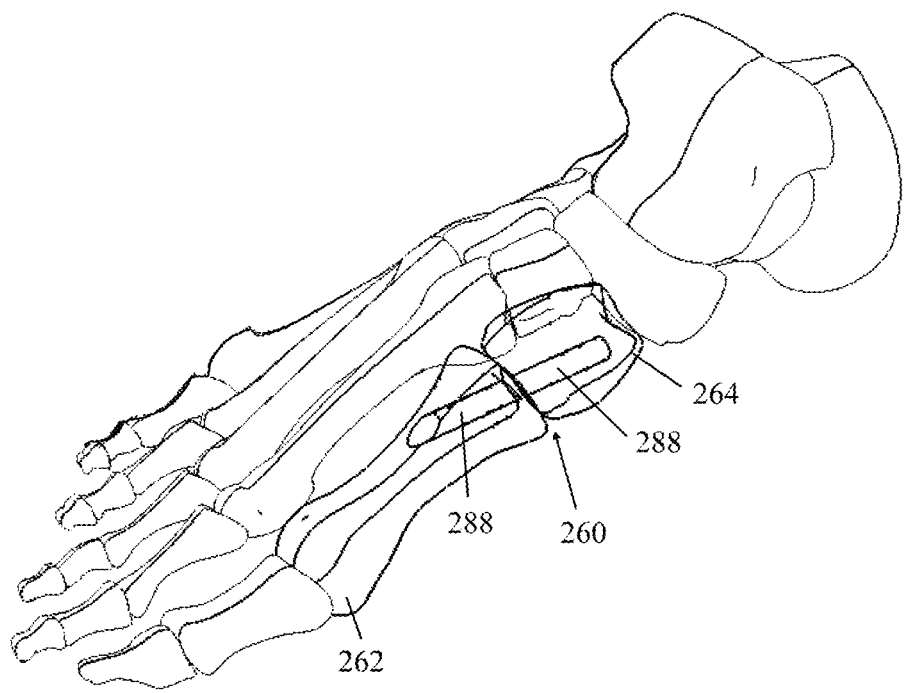
FIG. 17 is an isometric view of the foot of FIG. 16 showing the cavity for insertion of an intramedullary nail, in accordance with an aspect of the present invention.

A depth gauge (not shown) may then be used to measure the length of the guidewire 280 inserted into the bones 262, 264 to determine the length of intramedullary nail 200 needed. Once the length of the guidewire 280 that is inserted into the bones 262, 264 is determined three millimeters is subtracted from the measured length to account for compression of the joint 260. After subtracting three millimeters, the length of the intramedullary nail 200 that should be used is known. Next, in step 258, a drill may be used to drill over the guidewire 280 to create a cavity 288 for the intramedullary nail 200. The diameter of the drill used should correspond to the size of the intramedullary nail 200 that was selected for insertion into the joint 260. The drill may include measurement gradients lasered onto the drill bit to allow for reading of the depth drilled. Once the desired depth is reached to fit the selected intramedullary nail 200, the drill and guidewire 280 may be removed leaving cavity 288 for insertion of the intramedullary nail 200, as illustrated in FIG. 17.

Figure 18:
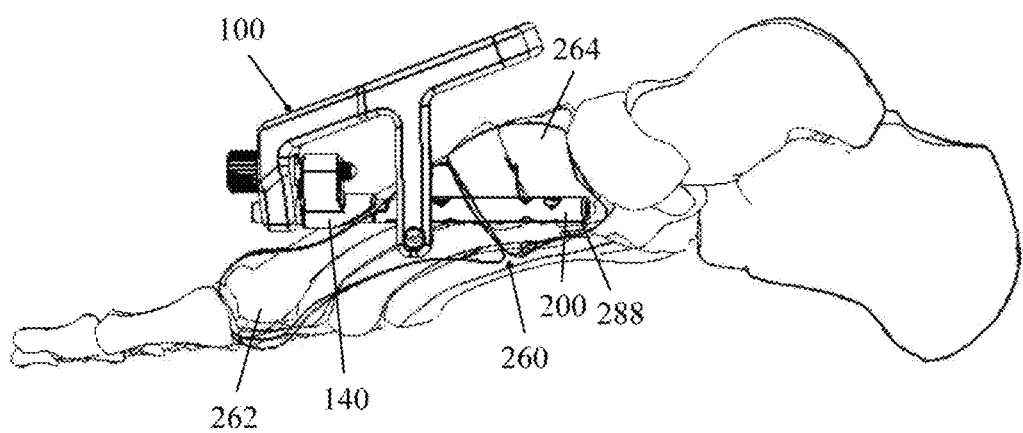
FIG. 18 shows a side view of the foot of FIG. 17 with an intramedullary nail inserted into the cavity, in accordance with an aspect of the present invention.

Next, in step 360, a fixation guide device 100 may be selected. Then in step 362, the nail 200 may be loaded onto the outrigger assembly 102 of the fixation guide device 100 by aligning the first step 180 and second step 182 of the nail attachment portion 128 with the second step 250 and the first step 248 of the nail 200, respectively. Once the nail attachment portion 128 and nail 200 are aligned, an engagement fastener 220 may be inserted into opening 126 to secure the nail 200 to the outrigger assembly 102 creating the fixation guide device 100 for use during insertion and fixation of the nail 200 into the cavity 288, as depicted in FIGS. 1 and 2. Referring now to FIG. 18, the fixation guide device 100 is then oriented to allow the surgeon to insert the nail 200 into the pre-drilled cavity 288. The nail 200 is advanced in the cavity 288 until a positive stop is reached on the guide device 100. When the nail 200 reaches the positive stop it will be countersunk in the cavity 288 approximately three millimeters (3 mm) preventing prominence of the nail 200 after compression has occurred and the nail 200 is in its final position.

Figure 19:
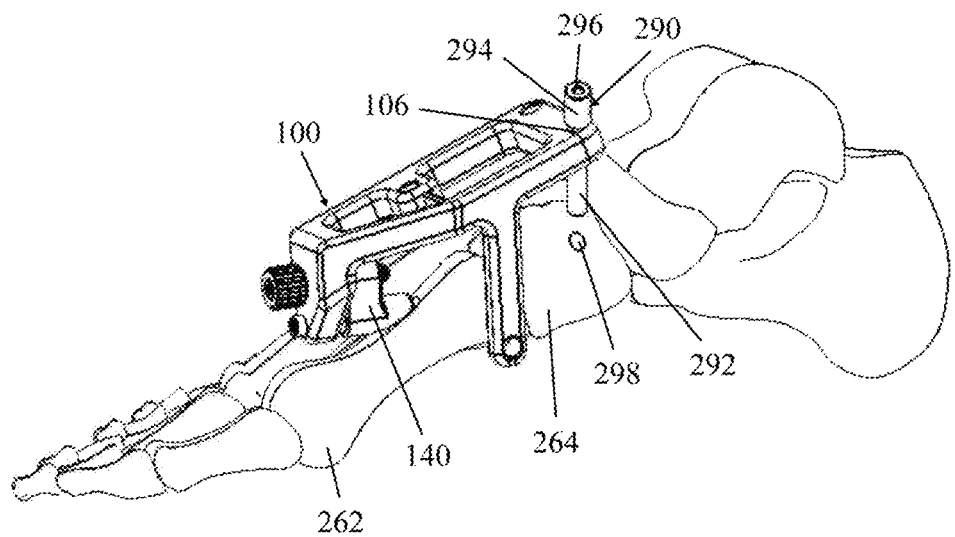
FIG. 19 shows an isometric side view of the embodiment of FIG. 18 including a drill sleeve inserted into a first position in the fixation guide, in accordance with an aspect of the present invention.
Figure 20:
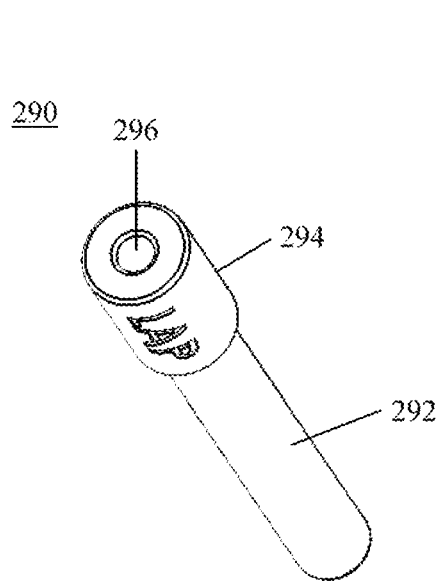
FIG. 20 shows an isometric view of the drill sleeve of FIG. 19, in accordance with an aspect of the present invention.
Figure 21:
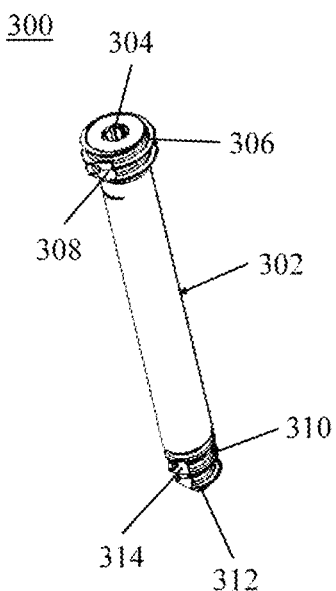
FIG. 21 is an isometric view of a peg for securing an intramedullary nail in the patient's foot, in accordance with an aspect of the present invention.
Figure 22:
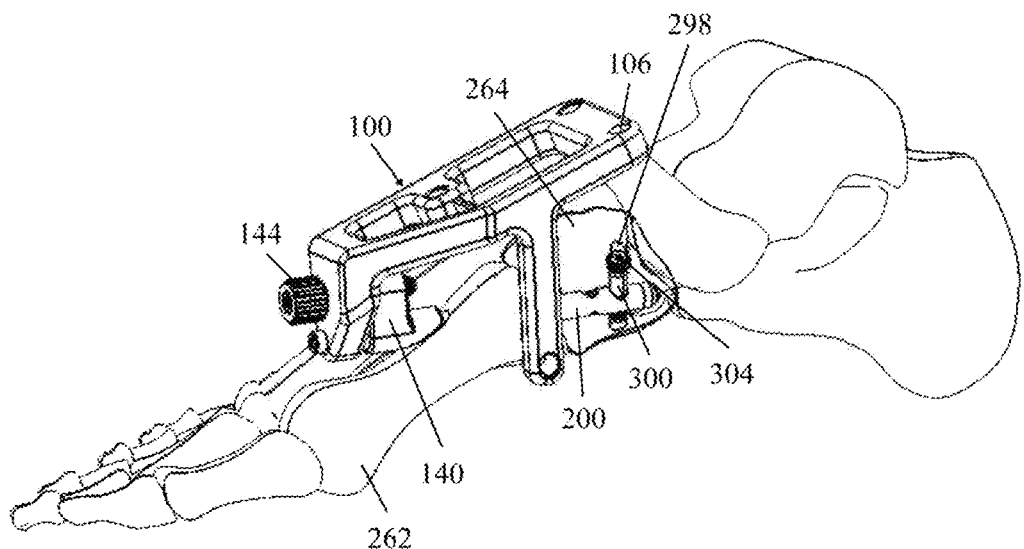
FIG. 22 shows a side isometric view of the embodiment of FIG. 19 including a first peg inserted into the patient's foot and the compression device for compressing the joint, in accordance with an aspect of the present invention.

Next, in step 366, as shown in FIG. 19, a drill sleeve 290 may be inserted into the first drill hole 106. The drill sleeve 290 including a sleeve portion 292 with a stop member 294 at the top and an opening 296 through the center of the sleeve portion 292, as depicted in FIG. 20. The opening 296 may have a diameter the size of the drill bit used to drill a cavity 298 in the second bone 264. The drill bit passes through the first opening 208 in the nail 200 when the cavity 298 is drilled. After the cavity 298 is drilled a depth gauge may be inserted into the cavity 298 through drill sleeve 290 to measure the depth of the cavity 298. Then the depth gauge and drill sleeve 290 may be removed from the first drill hole 106. Using the measured depth the surgeon may select a first peg 300 having the desired length. The first peg 300 may then be inserted through the first drill hole 106 and into the cavity 298, as shown in FIG. 22. The first peg 300 may be inserted relatively perpendicular to the nail 200. Referring now to FIG. 21, the pegs or fasteners 300, 320, 330, and 340 include a shaft 302 with a proximal end and a distal end. The proximal end includes a head 304, an upper threaded section 306, and a notch 308. In the depicted embodiment the head 304 is a hexagonal head although other head shapes, such as, a flat head, Phillips head, and the like are also contemplated. The distal end includes a lower threaded section 310 with a pointed end 312 and a notch 314. Between the proximal end and the distal end of the shaft 302 there may be a smooth region which mates with the first opening 208 of the nail 200. The upper threaded section 306 of the pegs 300, 320, 330, and 340 may be substantially flush with the exterior surface of the bones 262, 264. Alternatively, the pegs 300, 320, 330, and 340 may be countersunk below the surface of the bones 262, 264.

Figure 23:
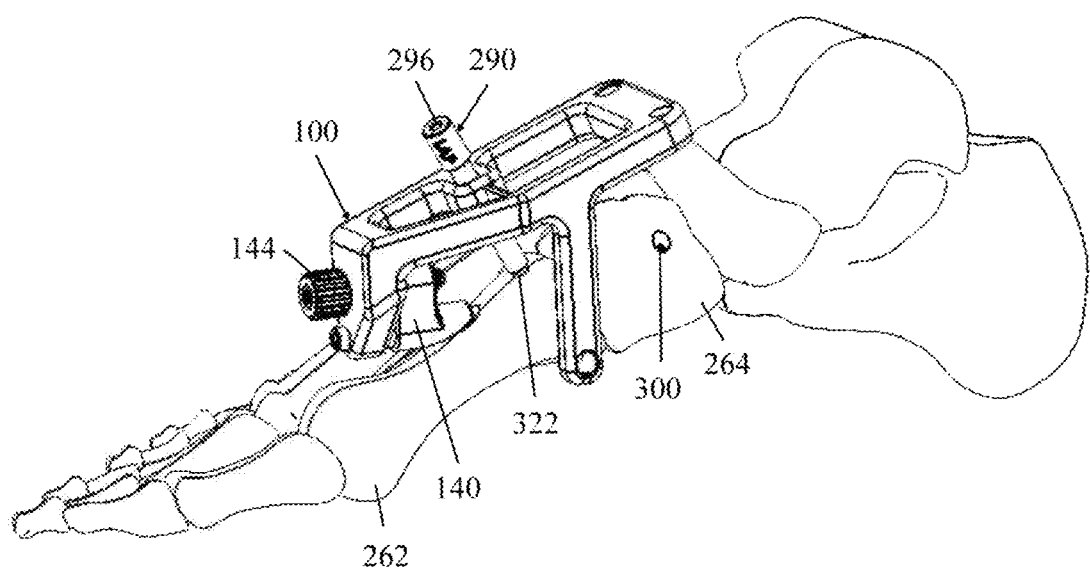
FIG. 23 is an isometric side view of the embodiment of FIG. 22 including a drill sleeve inserted into a second position in the fixation guide of FIG. 1, in accordance with an aspect of the present invention.
Figure 24:
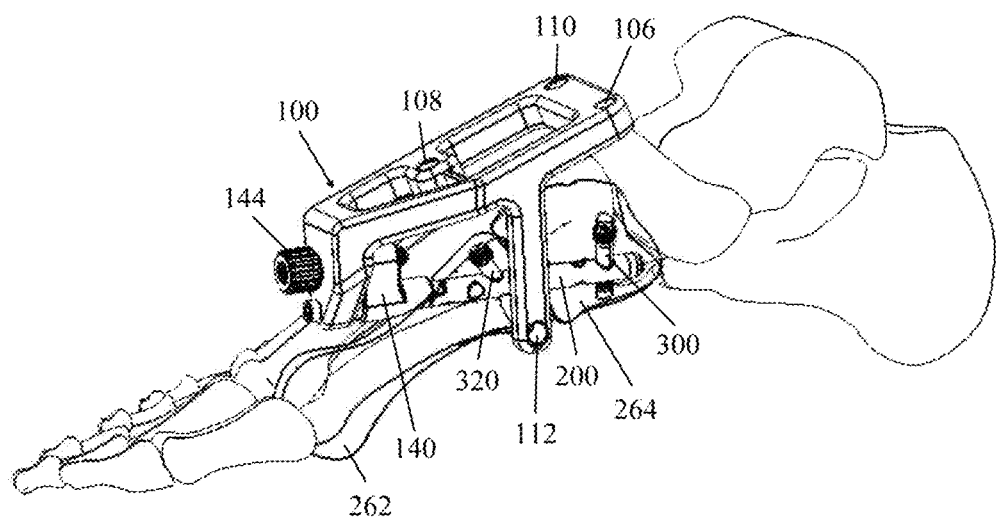
FIG. 24 is an isometric side view of the embodiment of FIG. 23 including a second peg inserted into the patient's foot, in accordance with an aspect of the present invention.

In step 368, the first peg 300 may then be used as a counter force for compression as knob 144 is turned forcing compression member 142 to move proximally and exert force on the first bone 262 as the first peg 300 holds the second bone 264 in place. As the compression member 142 is moved the first bone 262 and second bone 264 may be compressed at joint 260. Once the desired compression is achieved, next in step 370, a second peg 320 may be inserted by inserting the drill sleeve 290 into a second drill hole 108 and drilling a second cavity 322 into the first bone 262, as illustrated in FIG. 23. The second cavity 322 will pass through second opening 210 in the nail 200. After the second cavity 322 is drilled a depth gauge may be inserted into the second cavity 322 through drill sleeve 290 to measure the depth of the second cavity 322. Then the depth gauge and drill sleeve 290 may be removed from the second drill hole 108. Using the measured depth the surgeon selects a second peg 320 having the desired length. The second peg 320 may then be inserted through the second drill hole 108 and into the second cavity 322, as shown in FIG. 24. The second peg 320 may be inserted relatively perpendicular to the nail 200. The insertion of the second peg 320 will secure the achieved compression to prevent the loss of compression.

Figure 25:
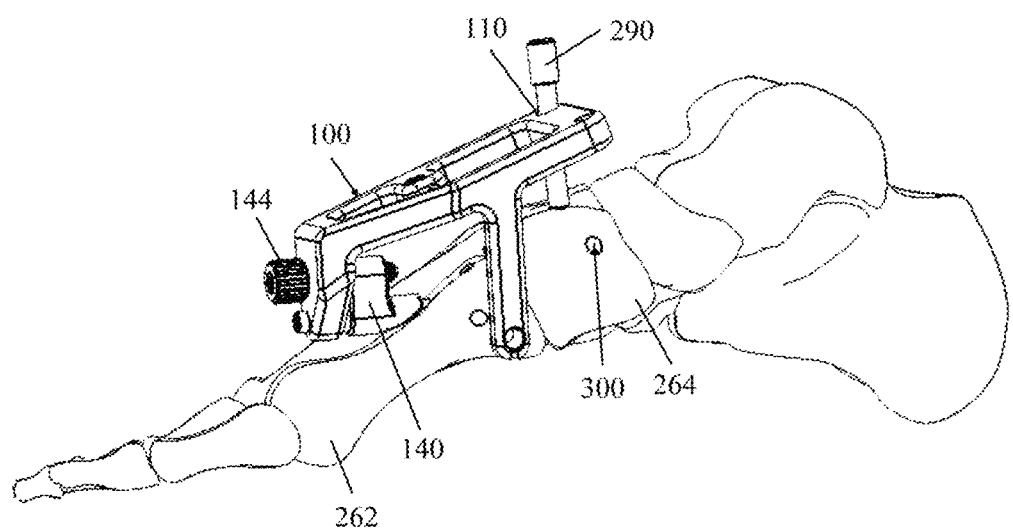
FIG. 25 is an isometric side view of the embodiment of FIG. 24 including a drill sleeve inserted into a third position in the fixation guide of FIG. 1, in accordance with an aspect of the present invention.
Figure 26:
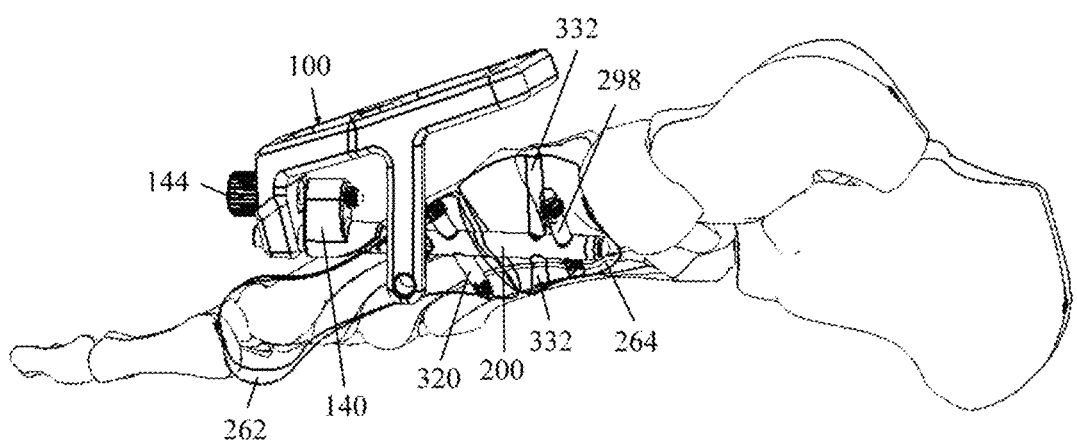
FIG. 26 is an isometric side view of the embodiment of FIG. 25 showing the opening for the third peg, in accordance with an aspect of the present invention.
Figure 27:
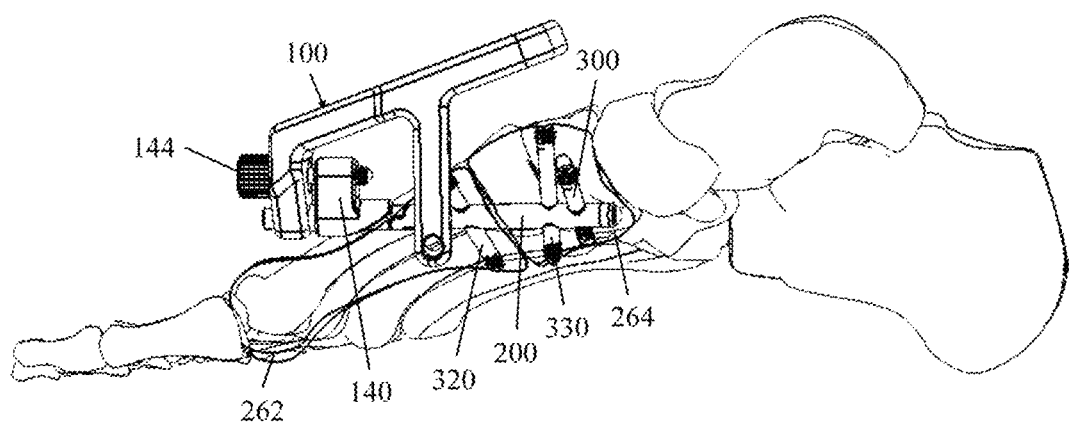
FIG. 27 is an isometric side view of the embodiment of FIG. 26 including a third peg inserted into the patient's foot, in accordance with an aspect of the present invention.

Referring now to FIG. 25, a drill sleeve 290 may be inserted into the third drill hole 110. A drill may then be inserted into opening 296 in drill sleeve 290 to drill a third cavity 332 into the second bone 264, as illustrated in FIG. 26. The third cavity 332 passes through the third opening 212 in the nail 200. After the third cavity 332 is drilled a depth gauge may be inserted into the third cavity 332 through drill sleeve 290 to measure the depth of the third cavity 332. Then the depth gauge and drill sleeve 290 may be removed from the third drill hole 110. Using the measured depth the surgeon may select a third peg 330 with the desired length. The third peg 330 may then be inserted through the third drill hole 110 and into third cavity 332, as shown in FIG. 27. The third peg 330 may be inserted relatively perpendicular to the nail 200. The insertion of the third peg 330 may add additional stability to the compression of the first bone 262 and second bone 264.

Figure 28:
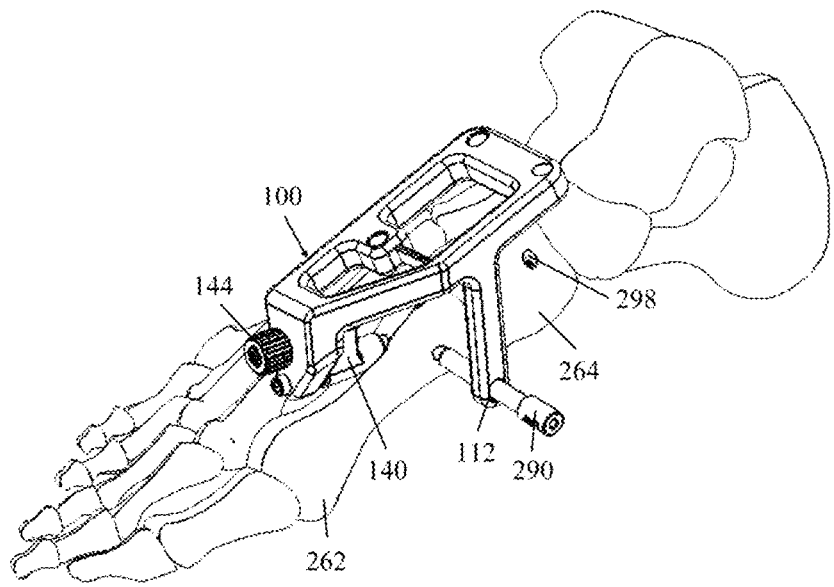
FIG. 28 is an isometric side view of the embodiment of FIG. 27 including a drill sleeve inserted into a fourth position in the fixation guide of FIG. 1, in accordance with an aspect of the present invention.
Figure 29:
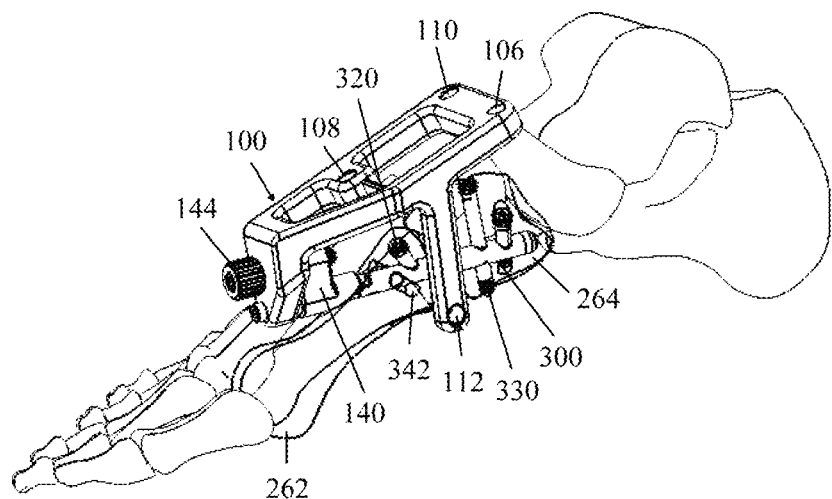
FIG. 29 is an isometric side view of the embodiment of FIG. 28 showing the fourth opening for the fourth peg, in accordance with an aspect of the present invention.
Figure 30:
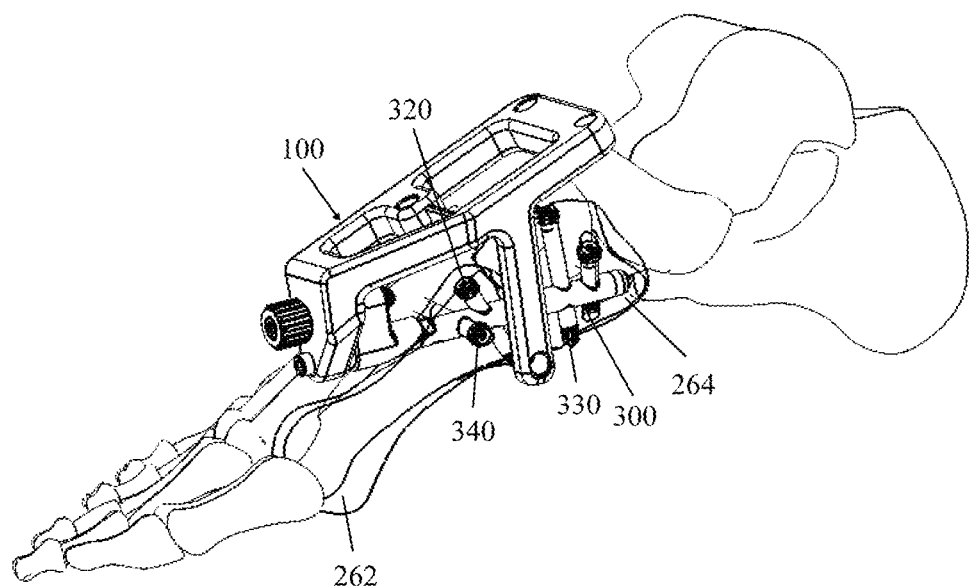
FIG. 30 is an isometric side view of the embodiment of FIG. 29 including a fourth peg inserted into the patient's foot, in accordance with an aspect of the present invention.

A drill sleeve 290 may be inserted into the fourth drill hole 112, as illustrated in FIG. 28. A drill may then be inserted into the opening 296 in the drill sleeve 290 to drill a fourth cavity 342 into the first bone 262. The fourth cavity 342, as best seen in FIG. 29, passes through the fourth opening 214 in the nail 200. After the fourth cavity 342 is drilled a depth gauge may be inserted into the fourth cavity 342 through drill sleeve 290 to measure the depth of the fourth cavity 342. Then the depth gauge and drill sleeve 290 may be removed from the fourth drill hole 112. Using the measured depth the surgeon may select a fourth peg 340 with the desire length. The fourth peg 340 may then be inserted through the fourth drill hole 112 and into the fourth cavity 342, as illustrated in FIG. 30. The fourth peg 340 may be inserted relatively perpendicular to the nail 200. The insertion of the fourth peg 340 may provide additional stability to the compression of the first bone 262 and the second bone 264.

Figure 31:
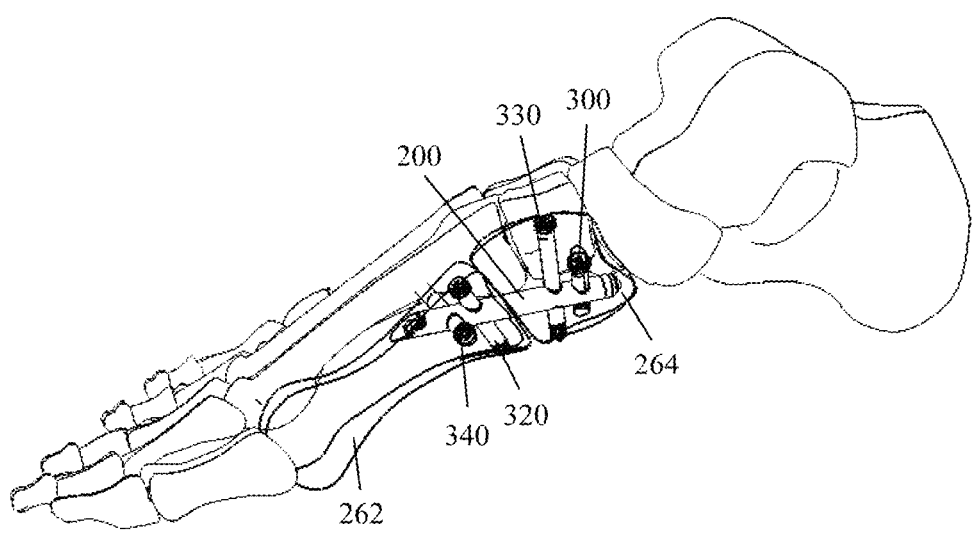
FIG. 31 is an isometric side view of the embodiment of FIG. 30 with the fixation guide of FIG. 1 removed, in accordance with an aspect of the present invention.
Figure 32:
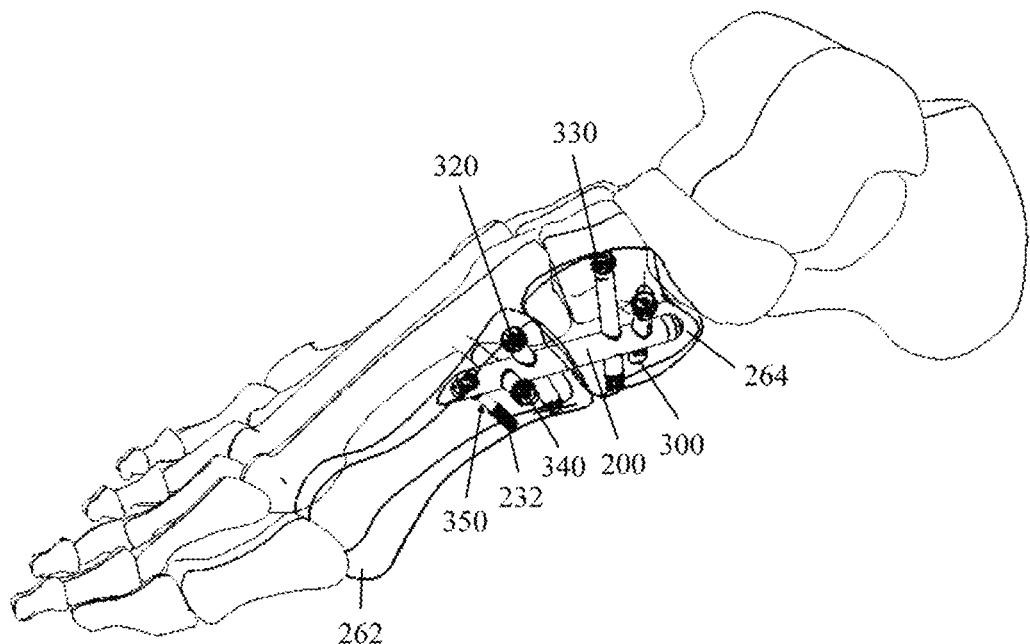
FIG. 32 is an isometric side view of the embodiment of FIG. 31 showing the locking screw inserted into an intramedullary nail, in accordance with an aspect of the present invention.

Next, in step 372, as shown in FIG. 31, after the four pegs 300, 320, 330, 340 are inserted into the first and second bones 262, 264, respectively, the outrigger assembly 102 may be detached from the nail 200 and removed from the foot. Next, in step 374, a locking drill guide may be threaded for inserting the locking screw 232 into the first bone 262 through the opening of the intramedullary nail 200. Once the locking drill guide is secured, a drill may be passed through an opening in the locking drill guide and the engagement opening 218 to create a cavity 350 for the locking screw 232. After the cavity 350 is drilled the locking drill guide may be removed. A depth gauge may then be inserted into the cavity 350 to measure the depth of the cavity 350. Using the measured depth the surgeon may select a locking screw 232. The selected locking screw 232 may then be inserted into the cavity 350 to secure the nail 200 in position in the first bone 262 and the second bone 264. After the locking screw 232 is inserted the position and stability of the nail 200 may be verified using fluoroscopy. Once the position of the nail 200 is verified a cap 252 may be inserted into the fastening end 206 to prevent bone ingrowth or overgrowth in order to maintain the ability to remove nail 200 if necessary or desired. The cap may include securing means to secure the cap to the nail 200 to prevent disengagement of the cap. Next, in step 376, the incision over the joint 260 may be closed by the surgeon.

Figure 33:
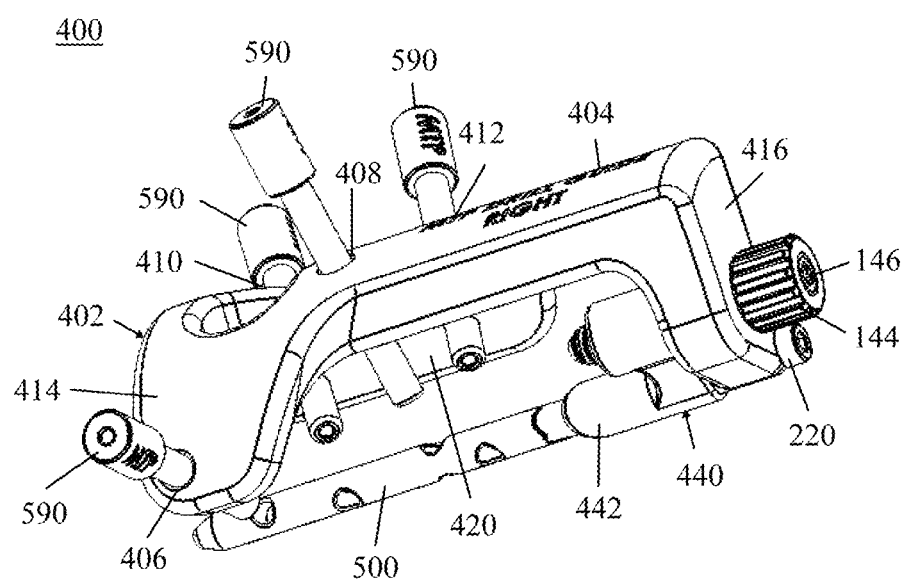
FIG. 33 shows an isometric view from the medial side of another fixation guide, in accordance with an aspect of the present invention.
Figure 34:
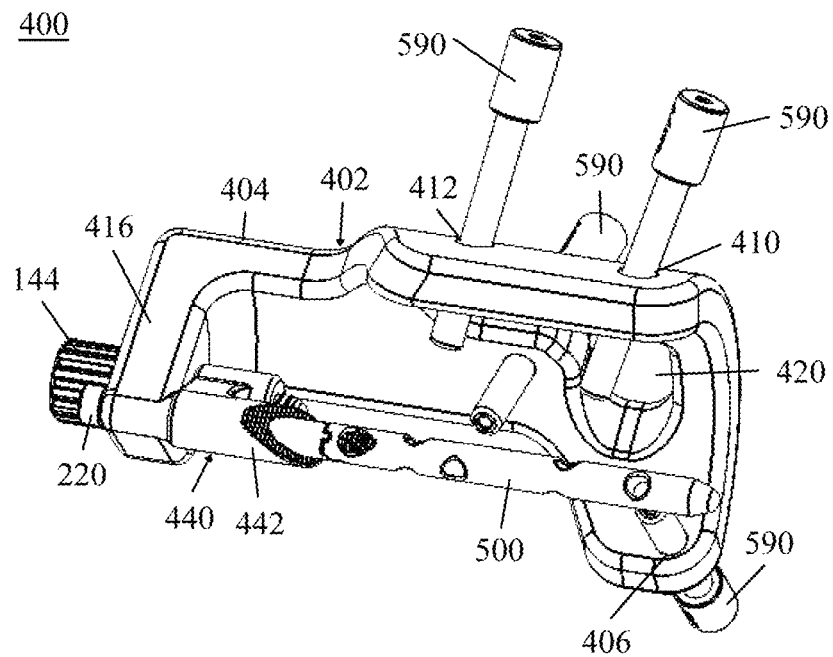
FIG. 34 shows an isometric view from the lateral side of the fixation guide of FIG. 33, in accordance with an aspect of the present invention.
Figure 35:
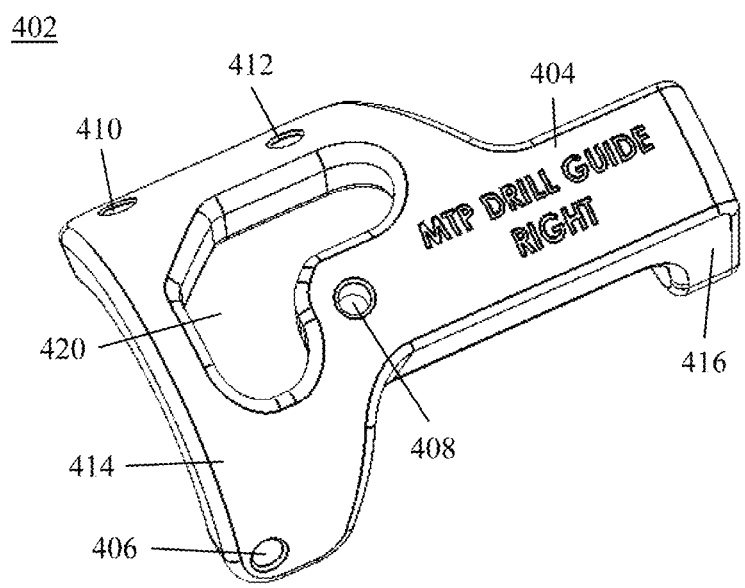
FIG. 35 is an isometric view from the top-medial side of an outrigger assembly of the fixation guide of FIG. 33, in accordance with an aspect of the present invention.
Figure 36:
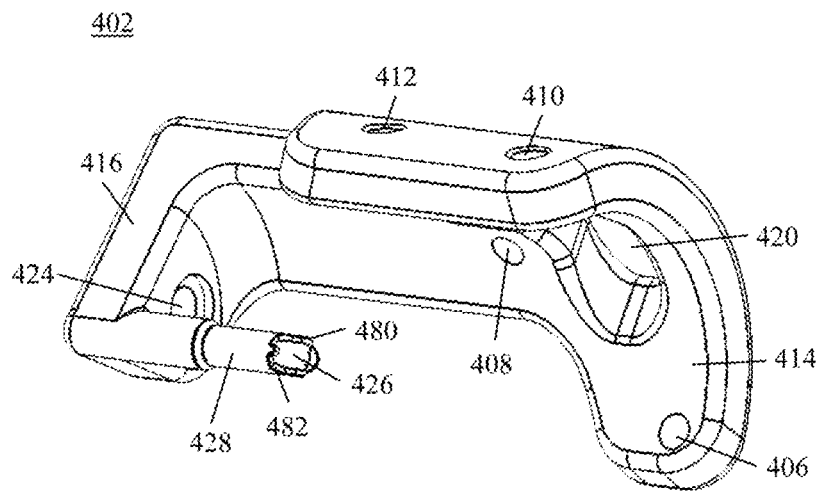
FIG. 36 is an isometric view from the bottom-lateral side of the outrigger assembly of FIG. 4, in accordance with an aspect of the present invention.

Referring now to FIGS. 33-54, with specific reference to FIGS. 33 and 34 showing an exemplary embodiment fixation guide device 400. The fixation guide device 400 may include an outrigger assembly or frame 402, a compression device 440, and an intramedullary nail 500. The outrigger assembly 402, shown in FIGS. 35 and 36, includes a base 404 with a lateral wing or outwardly extending wing 414 including a first drill hole 406, a second drill hole 408, a third drill hole 410, a fourth drill hole 412, and a proximal arm 416. It is also contemplated that the frame 402 may include, for example, a plurality of drill holes to correspond to the number of openings in an intramedullary nail, for example, nail 200, 500, 700 in order to secure the intramedullary nail to the patient's bones. The drill holes 406, 408, 410, 412 may each include, for example, multiple holes spaced a small distance apart or multiple nested or overlapping holes to correspond to the openings 508, 510, 512, 514 in various sized intramedullary nails 500. The base 404 may include at least one opening 420 allowing for visualization through the base 404 with imaging technology, such as x-ray. The proximal arm 416 is perpendicular to the base 404 at a proximal end of the outrigger assembly 402 and includes a knob opening 424, a nail attachment opening 426, and a nail attachment portion 428. The nail attachment portion 428 may include an end with an inverted two step profile including a first step or nail attachment segment 480 and a second step or nail attachment segment 482. The base 404 may ideally be made of a material that is strong enough to prevent deformation during surgery, such as, a metal, while also being radiolucent, for example, carbon fiber, to allow for imaging through the base 404 to determine whether correct alignment of the nail 500 was achieved.

Figure 37:
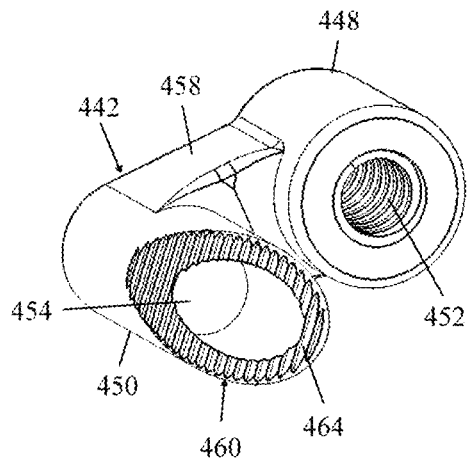
FIG. 37 is a front isometric view of a compression member of the fixation guide of FIG. 33, in accordance with an aspect of the present invention.
Figure 38:
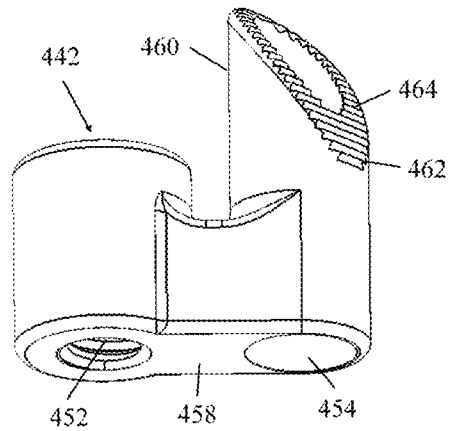
FIG. 38 is a top isometric view of the compression member of FIG. 37, in accordance with an aspect of the present invention.

The compression device 440 slidingly mates with the nail attachment portion 428. The compression device 440 includes a compression member 442, a knob 444, and a bolt 446. As best seen in FIGS. 37-38, the compression member 442 has a base 458 with a top end 448 and a bottom end 450. The compression member 442 also includes a protrusion 460 at the bottom end 450, a first opening 452 near the top end 448 for receiving the bolt 446, and a second opening 454 near the bottom end 450 passing through the base 458 and protrusion 460. The compression member 442 may be of the type described above with reference to the compression member 142 and will not be described again here for brevity sake The second opening 454 is slidingly engaged with the nail attachment portion 428. The compression member 442 may also include a midpoint 462 and teeth 464 on the angled portion of the protrusion 460, as described above with reference to compression member 142.

As depicted, after the compression member 442 is slid over nail attachment portion 428, the knob 144 may be secured to the base 404 using a bolt 146 and fastener inserted into opening 170. The knob 144, shown in FIG. 7, and the bolt 146, illustrated in FIG. 8, are both described above with reference to the fixation guide device 100. The threaded end 156 of bolt 146 may be inserted into the knob opening 424 and the threaded end 156 mates with the threads of the second opening 454. The stop member 166 of the bolt 146 may prevent the bolt 146 from passing through the knob opening 424.

Figure 39:
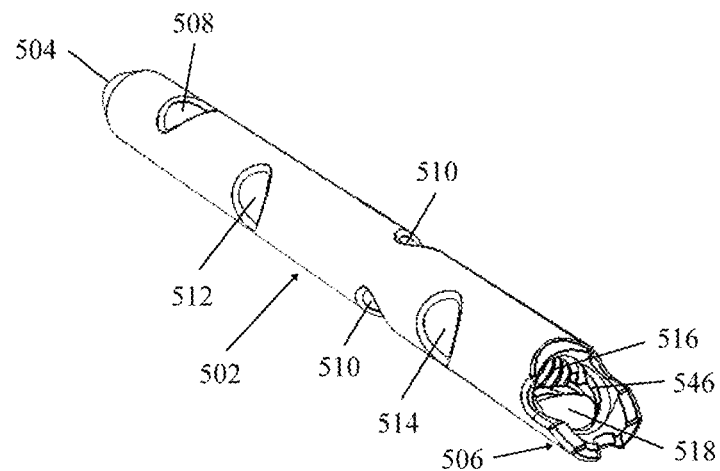
FIG. 39 is an isometric view of an embodiment of an intramedullary nail of the fixation guide of FIG. 33, in accordance with an aspect of the present invention.
Figure 40:
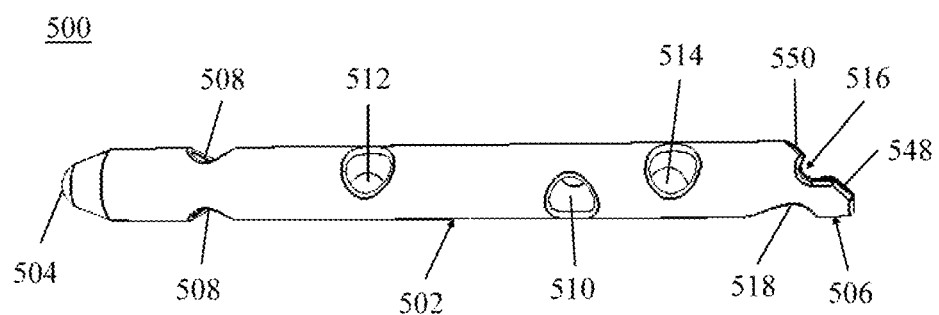
FIG. 40 is a side view of the intramedullary nail of FIG. 39, in accordance with an aspect of the present invention.

Referring now to FIGS. 39-40 with continued reference to FIGS. 33-34, the intramedullary nail 500 may be of the type described above with reference to nail 200 and may include a body 502 with a closed end 504, a fastening end 506 with an insertion opening 516 and an engagement opening 518, and four openings 508, 510, 512, 514. It is also contemplated that the intramedullary nail 500 may include any number of openings 508, 510, 512, 514 as may be necessary to secure the nail to a patient's bones. The insertion opening 516 may be used to secure the nail 500 to the nail attachment portion 428 using an engagement fastener 220, for example, a screw, such as the one illustrated in FIG. 11.

Figure 41:
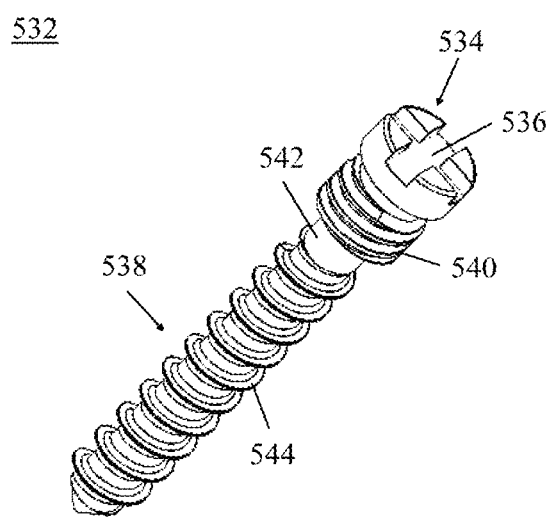
FIG. 41 is an isometric view of an intramedullary nail locking screw of the fixation guide of FIG. 33, in accordance with an aspect of the present invention.

The engagement opening 518 may be a threaded opening, with threads 546, that passes through the exterior surface of nail 500 to secure the nail 500 to the bone using a locking screw 532. The locking screw 532, as depicted in FIG. 41, may include a head 534 with a drive opening 536 and a shank 538 with a first threaded section 540, a smooth section 542, and a second threaded section 544, as described above with reference to locking screw 232 and which will not be described again here for brevity sake.

The nail 500 may also include a fastening end 506 with a shape that corresponds to the shape of the end of the nail attachment portion 428 to create a tight fit between the nail 500 and the attachment portion 428. As depicted in FIGS. 39-40, the fastening end 506, may be of the type described above with reference to fastening end 206, and includes a two step profile including a first step or fastening segment 548 and a second step or fastening segment 550. Thus, the nail 500 may be secured to the outrigger assembly 402, as described above with reference to FIGS. 9-10.

The surgical method for inserting the intramedullary nail 500 into a patient's joint 560 may include the steps of FIG. 55, as illustrated in FIGS. 42A-54. The method utilizes some of the devices, instruments, features, aspects, components, and the like described above with reference to the fixation guide device 400, and therefore reference will be made to the above described embodiments illustrated in FIGS. 33-41 and discussed above. However, such references are made for exemplary purposes only and are not intended to limit the surgical method beyond the specifically recited steps. Further, the surgical method may be discussed under the umbrella of particular bones, but such an application is not intended to be limiting and the method described herein may be used or conducted with bone or other tissue not specifically discussed herein without departing from the spirit and scope of the surgical method.

If a joint 560, for example, a metatarsal phalangeal joint or the like, needs to be surgically fixed, a surgeon would first expose the joint 560 by creating an incision over the joint 560 as in step 352. Next, in step 354, the first bone 262 and the third bone 564 of the joint 560 will be prepared by using a cut guide and cartilage removal technique such as a curet, osteotome, saw blade, or other similar cartilage removal technique known by one skilled in the art. The joint 560 is then aligned by moving the first bone 262 and third bone 564 into a desired position for fixation. Once the bones 262, 564 are aligned, temporary fixation may be applied to hold the joint 560 in the desired position. A guidewire, template, or similar clamp may be used to temporarily fix the joint 560.

Figure 42A:
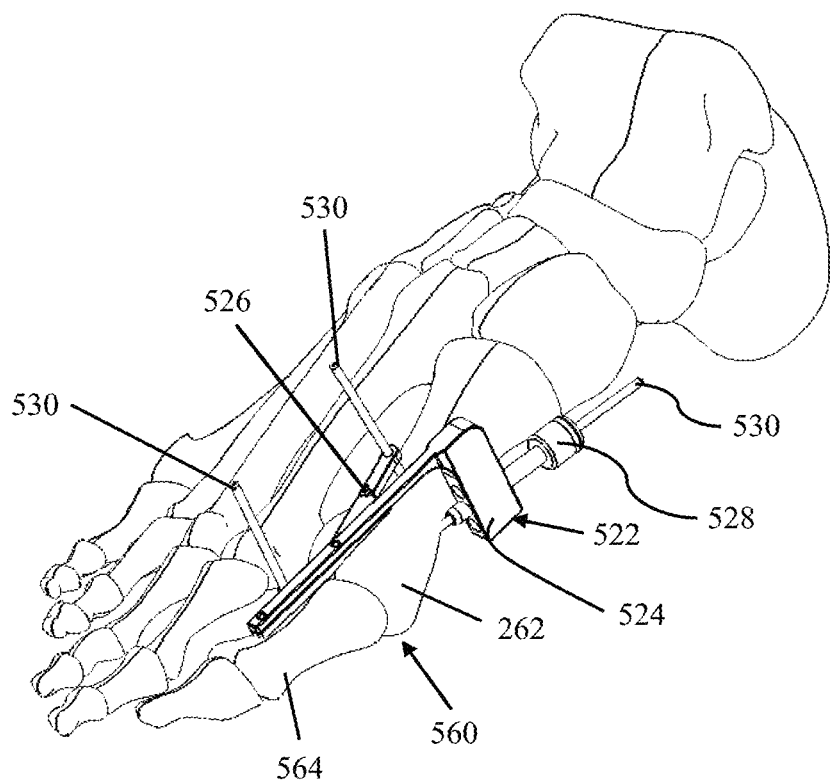
FIG. 42A is an isometric view of a guidewire alignment guide mounted onto a patient's foot with guidewires, in accordance with an aspect of the present invention.
Figure 42B:
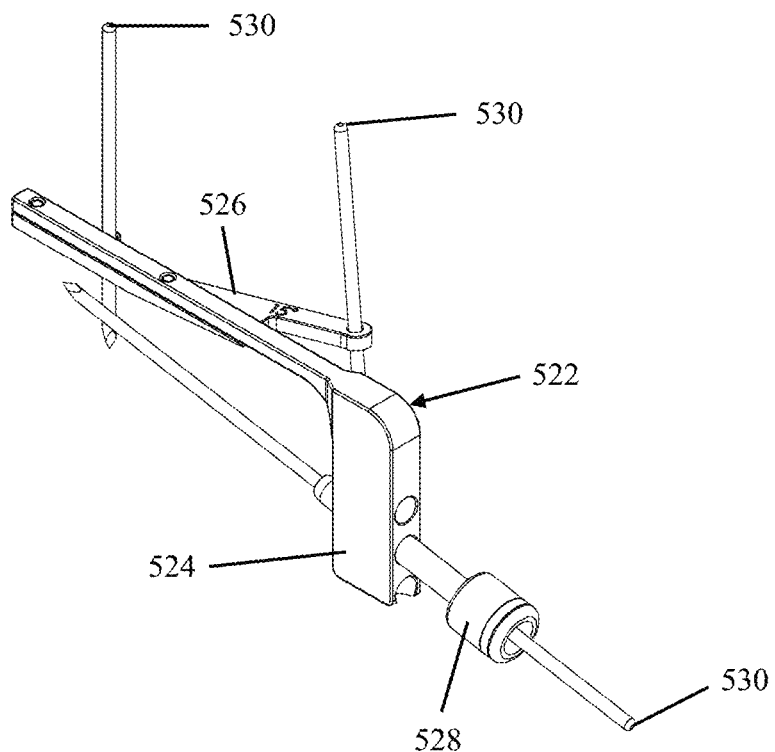
FIG. 42B is an isometric left side view of the guidewire alignment guide and guidewires of FIG. 42A, in accordance with an aspect of the present invention.
Figure 42C:
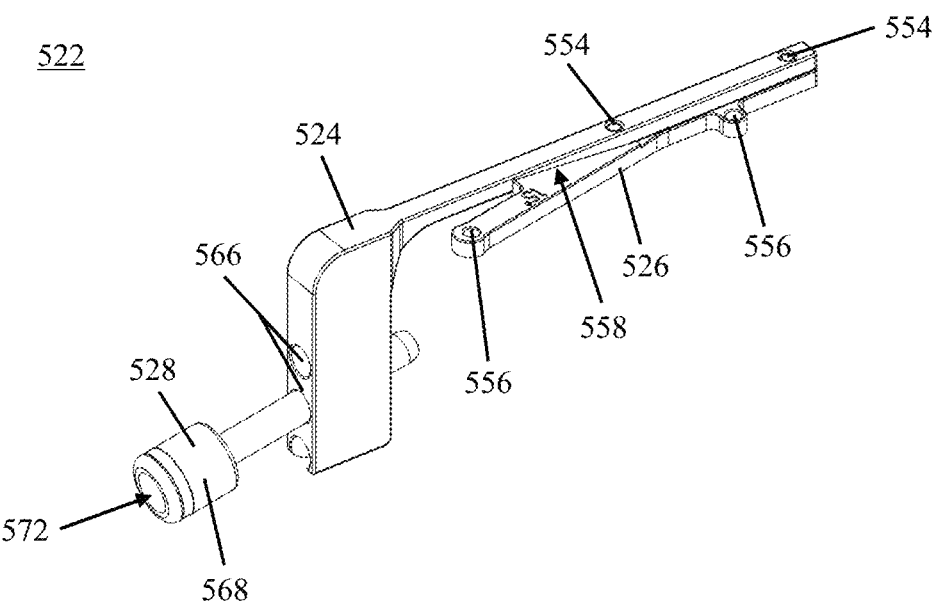
FIG. 42C is an isometric right side view of the guidewire alignment guide of FIG. 42A, in accordance with an aspect of the present invention.
Figure 42D:
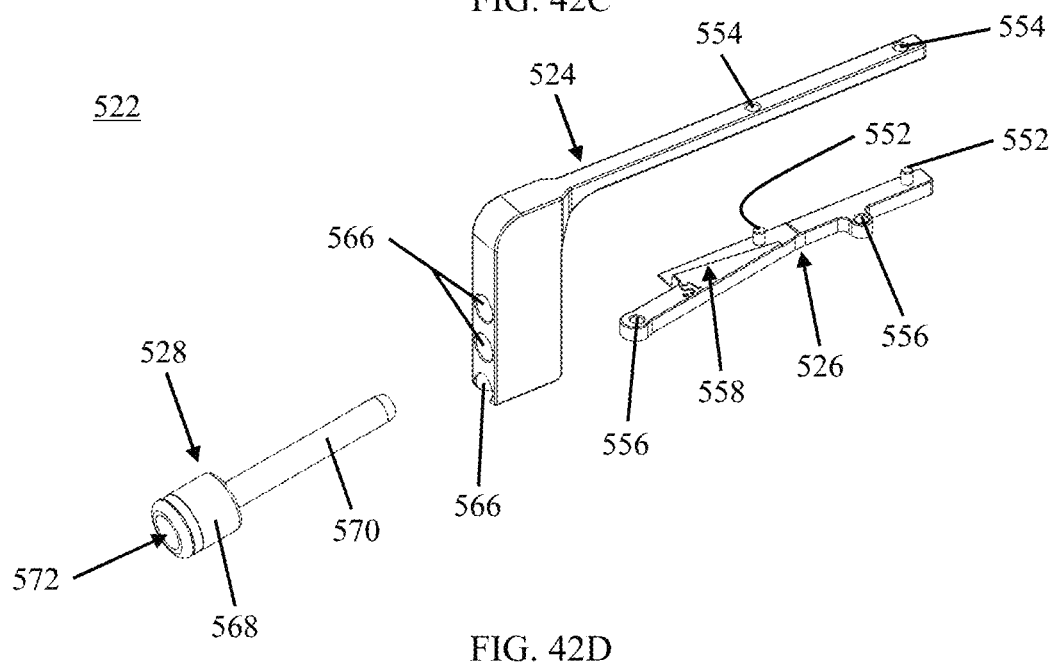
FIG. 42D is an exploded view of the guidewire alignment guide of FIG. 42A, in accordance with an aspect of the present invention.
Figure 42E:
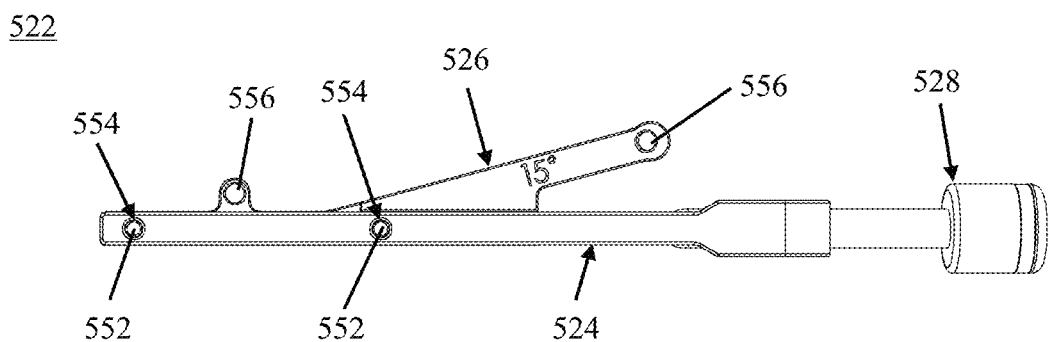
FIG. 42E is a top view of the guidewire alignment guide of FIG. 42A, in accordance with an aspect of the present invention.
Figure 42F:
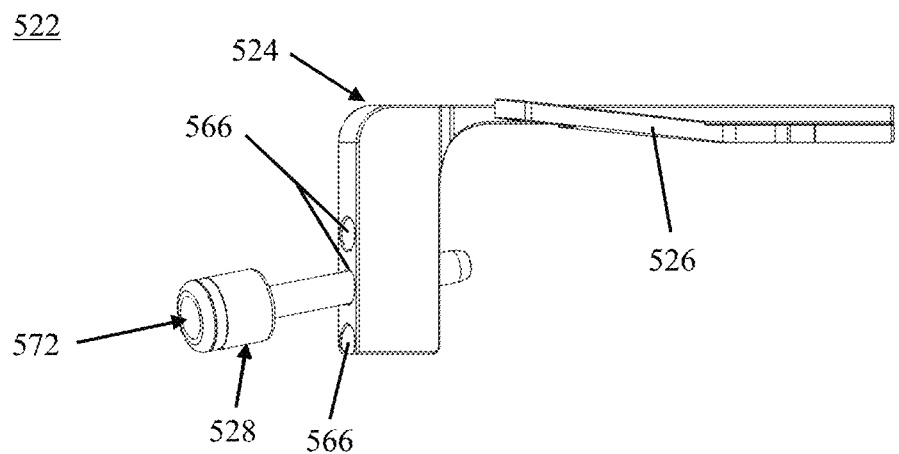
FIG. 42F is a side view of the guidewire alignment guide of FIG. 42A, in accordance with an aspect of the present invention.

Next, in step 356, shown in FIG. 42A, an alignment guide 522, as illustrated in FIGS. 42B-42F, is aligned with the patient's first bone 262 and third bone 564. The alignment guide 522 includes a base member 524 with an alignment member 526 and a fixation guide or temporary fixation guide 528. The base member 524 includes a first member and a second member. The alignment member 526 couples to the base member 524 for alignment of the first bone 262 and the third bone 564. The alignment member 526 may be coupled to the base member 524 by, for example, pins 552 on the alignment member 526 which engage openings 554 on the base member 524, as shown in FIG. 42D. When the alignment member 526 is coupled to the base member 524 the alignment portion 558 aligns the alignment member 526 relative to the second member of the base member 524. The alignment portion 558 may be angled at a desired angle, which may range from, for example, approximately 0 degrees to 25 degrees and more preferably from approximately 10 degrees to 15 degrees. The alignment portion 558 allows a surgeon to maintain the desired alignment of the first bone 262 and third bone 564 of the patient's toe.

Once the guide 522 is aligned, at least two guidewires 530 may be inserted into through holes or openings 556 to temporarily fix the guide 522 to the first bone 262 and third bone 564. After temporarily fixing the guide 522 to the first and third bones 262, 564 the fixation guide 528 may be inserted into one of the holes 566 in the first member of the base member 524 providing the desired path through the patient's joint. The fixation guide 528 may include a head 568, a shaft 570 extending out from the head 568 and a through hole 572 extending through the center of the head 568 and the shaft 570. After inserting the fixation guide 528 into the desired hole 566 a guidewire 530 may be inserted into the through hole 572 of the temporary fixation guide 528 and into the bone 262 and third bone 564 across the joint. The guidewire 530 inserted into the temporary fixation guide 528 may be positioned to be used as a drilling guide for the intramedullary nail 500. Once the guidewire 530 is inserted across the joint 560 the alignment guide 522 may be removed, leaving the guidewire 530 in position for drilling a cavity for the nail 500.

Figure 43A:
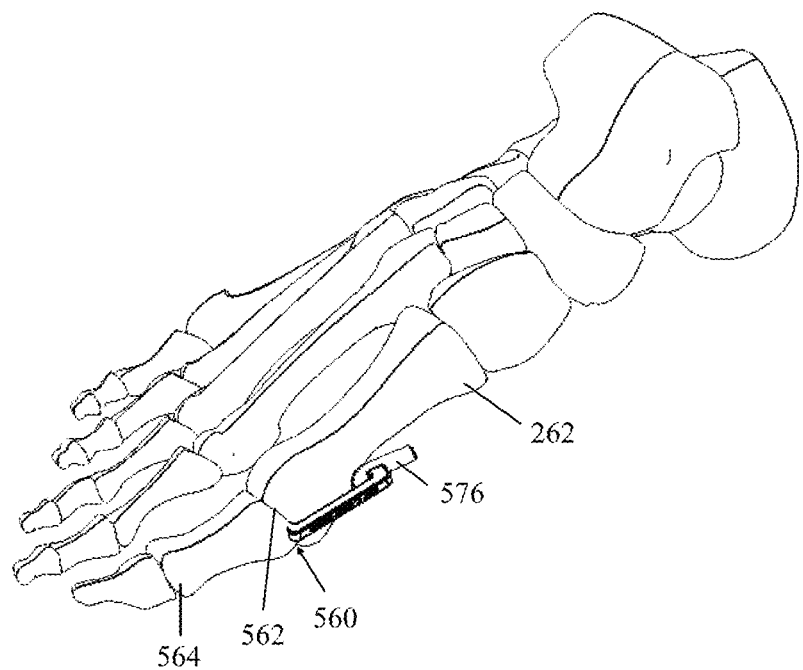
FIG. 43A is an isometric view of another guidewire alignment guide mounted onto a foot of a patient, in accordance with an aspect of the present invention.
Figure 43B:
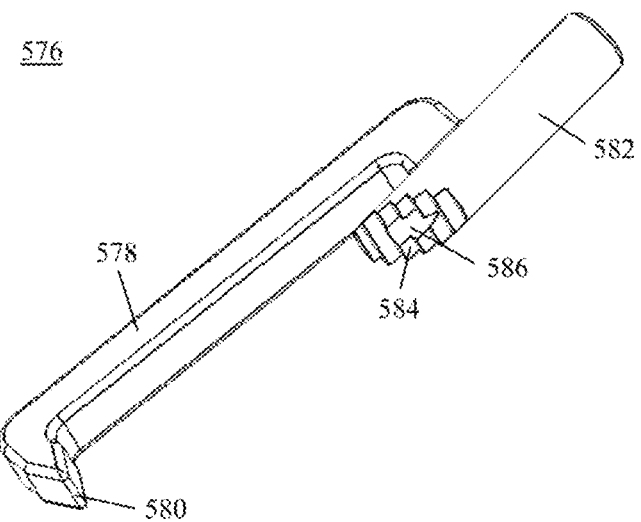
FIG. 43B is a side isometric view of the guidewire alignment guide of FIG. 43A, in accordance with an aspect of the present invention.

Alternatively, step 356 may be performed as shown in FIG. 43A, using the alignment guide 576, as illustrated in FIG. 43B, wherein the guide 576 is aligned with the patient's first bone 262. The alignment guide 576 includes a body 578 with a distal end which includes a pointed end 580 and a drill guide portion 582 at the proximal end of the body 578. The drill guide portion 582 includes a bone mating portion 584 and a center channel 586 for the drill to pass through. The pointed end 580 aligns with the distal end of the first bone 262. Once the guide 576 is aligned, a guidewire may be inserted through a center channel 586 and into the distal end 562 of the first bone 262 and the third bone 564. The guidewire may be positioned to be used as a drilling guide for the intramedullary nail 500. Once the guidewire is inserted across the joint 560 the alignment guide 576 may be removed, leaving the guidewire in position for drilling a cavity for the nail 500.

Figure 44:
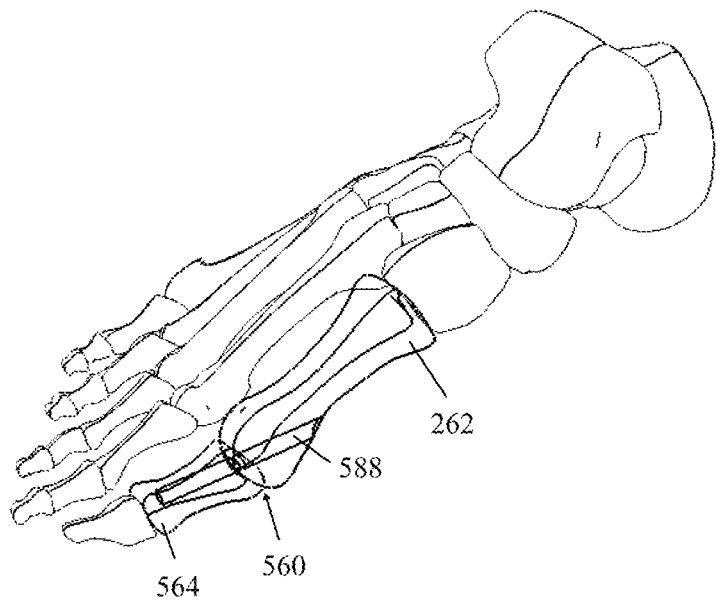
FIG. 44 is an isometric view of the foot of FIG. 42A showing the cavity for insertion of the intramedullary nail of FIG. 39, in accordance with an aspect of the present invention.

A depth gauge (not shown) may then be used to determine the length of the intramedullary nail 500 to be used, as described above with reference to determining the length of nail 200, which will not be described again here for brevity sake. Next, in step 358, a cavity 588 for the nail 500 is drilled, as described above with reference to drilling cavity 288, and nail 500 is inserted, as illustrated in FIG. 44.

Figure 45:
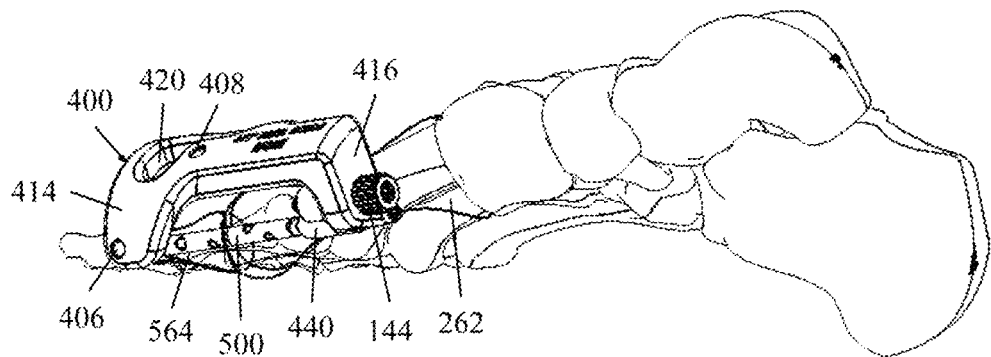
FIG. 45 shows a side view of the foot of FIG. 44 with the intramedullary nail of FIG. 39 inserted into the cavity, in accordance with an aspect of the present invention.

Next, in step 360, a fixation guide device 400 may be selected. Then, in step 362, as depicted in FIGS. 33 and 34, the nail 500 may then be loaded onto the outrigger assembly 402 creating the fixation guide device 400 for use during insertion and fixation of the nail 500 into the cavity 588, as described above with reference to nail 200 and outrigger assembly 102. Next, in step 364, as shown in FIG. 45, the fixation guide device 400 may then be oriented to allow the surgeon to insert the nail 500 into the pre-drilled cavity 588, as described above with reference to insertion of nail 200, which will not be described again here for brevity sake. The nail 500 may be countersunk in the cavity 588, approximately two to three millimeters depending on pre-operative assessment.

Figure 46:
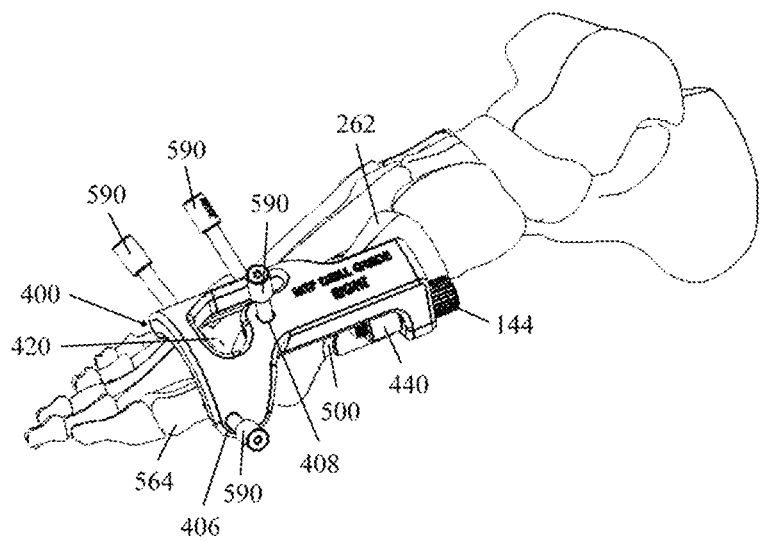
FIG. 46 shows an isometric side view of the embodiment of FIG. 45 including the four drill sleeves inserted into the drill holes of the fixation guide of FIG. 35, in accordance with an aspect of the present invention.
Figure 47:
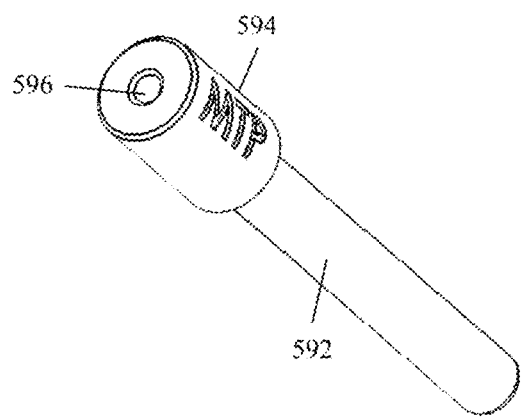
FIG. 47 shows an isometric view of the drill sleeves of FIG. 46, in accordance with an aspect of the present invention.

Referring now to FIG. 46, drill sleeves 590 are shown inserted into a first drill opening 406, a second drill opening 408, a third drill opening 410, and a fourth drill opening 412 of the base 404. The drill sleeves 590 include a sleeve portion 592 with a stop member 594 at the top and an opening 596 through the center of the sleeve portion 592, as depicted in FIG. 47. The diameter of the opening 596 may be the same size as the drill bit used to drill cavities into the first and second bones 262, 564. The cavities are drilled through the opening 596 in the drill sleeve 590 and the openings 508, 510, 512, and 514 in the nail 500.

Figure 48:
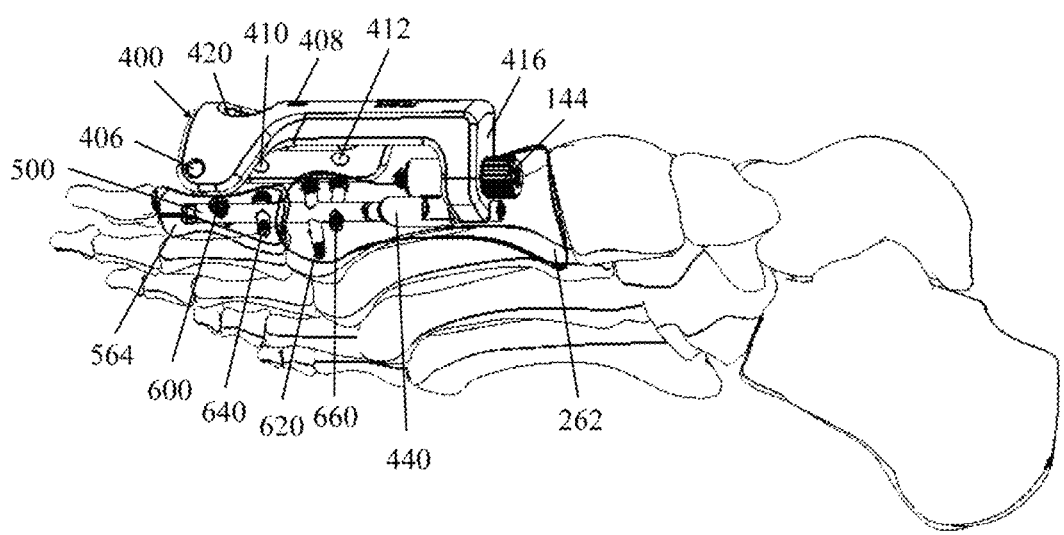
FIG. 48 is a side isometric view of the embodiment of FIG. 46 showing the four pegs inserted into the patient's foot, in accordance with an aspect of the present invention.
Figure 49:
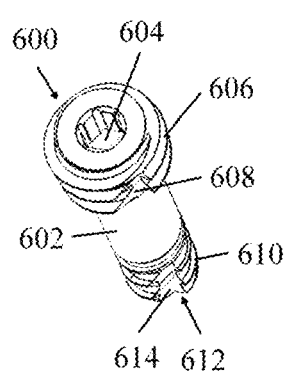
FIG. 49 is an isometric view of a first peg for securing the intramedullary nail of FIG. 39 in the patient's foot, in accordance with an aspect of the present invention.
Figure 50:
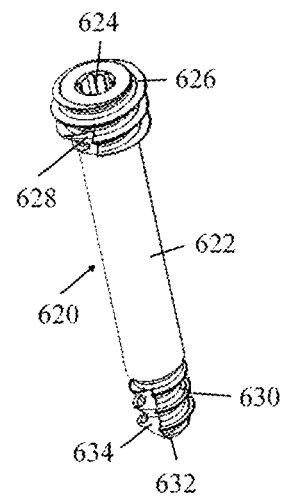
FIG. 50 is an isometric view of a second peg for securing the intramedullary nail of FIG. 39 in the patient's foot, in accordance with an aspect of the present invention.
Figure 51:
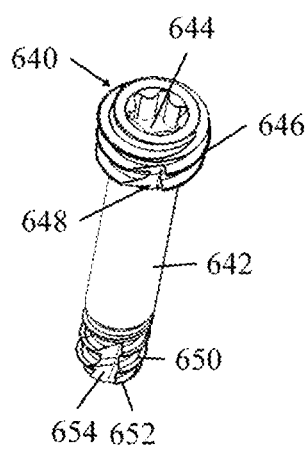
FIG. 51 is an isometric view of a third peg for securing the intramedullary nail of FIG. 39 in the patient's foot, in accordance with an aspect of the present invention.
Figure 52:
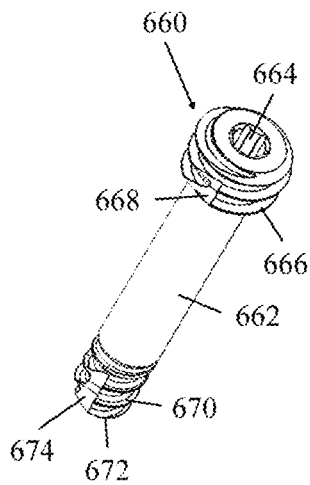
FIG. 52 is an isometric view of a fourth peg for securing the intramedullary nail of FIG. 39 in the patient's foot, in accordance with an aspect of the present invention.

Referring now to FIGS. 46 and 48, the nail 500 is shown fixed into the bones 262, 564 using four pegs or fasteners 600, 620, 640, and 660. Referring now to FIGS. 49-52, the first peg 600, second peg 620, third peg 640, and fourth peg 660 each include a shaft 602, 624, 644, 664, respectively, with a proximal end and a distal end. The proximal ends include a head 604, 626, 646, 666, an upper threaded section 606, 628, 648, 668, and a notch 608, 630, 650, 670. In the depicted embodiment the heads 604, 626, 646, 666 may be hexagonal heads, although other head shapes, such as, a flathead, Phillips head, other multi-lobed configurations, and the like are also contemplated. The distal ends include a lower threaded section 610, 632, 652, 672 with a pointed end 612, 634, 654, 674 and a notch 614, 636, 656, 676. Between the proximal ends and distal ends of the shafts 602, 624, 644, 664 there may be a smooth region which mates with the first opening 508, second opening 510, third opening 512, fourth opening 514, respectively, of the nail 500.

Once the nail 500 is inserted into the cavity 588 it will be secured to the bones 262, 564 using at least two pegs, in the depicted embodiment four pegs 600, 620, 640, and 660 are used. Next, in step 366, as shown in FIG. 48, the surgeon may secure the nail 500 by inserting the first peg 600 into a first cavity 598 in the third bone 564, as described above with reference to drilling, measuring, and inserting the first peg 300, which will not be described again here for brevity sake.

Next, in step 368, the first peg 600 may then be used as a counter force for compression as knob 144 is turned forcing compression member 442 to move distally and exert force on the first bone 262 as the first peg 600 holds the third bone 564 in place. As compression member 442 is moved the first bone 262 and third bone 564 are compressed at joint 560. Once the desired compression has been achieved, in step 370, a second peg 620 may be inserted using drill sleeve 590 to drill a second cavity 622 in the first bone 262, as described above with reference to second cavity 322. After the second cavity 622 is drilled the depth of the cavity 622 may be measured and the length of a second peg 620 selected, as described above with reference to second peg 320 which will not be described again here for brevity sake. The second peg 620 may then be inserted through the second drill opening 408 and into the second cavity 622, as shown in FIG. 48. The insertion of the second peg 620 may secure the achieved compression to prevent the loss of compression.

With continued reference to FIGS. 46 and 48, the drill sleeve 590 may also be inserted into the third drill hole 410. A drill may then be inserted into opening 596 in the drill sleeve 590 to drill a third cavity 642 into the third bone 564. The third cavity 642 may pass through the third opening 512 in nail 500. After the third cavity 642 is drilled a depth gauge may be inserted into the third cavity 642 through the drill sleeve 590 to measure the depth of the third cavity 642. Then the depth gauge and the drill sleeve 590 may be removed from the third drill opening 410. Using the measured depth, the surgeon may select a third peg 640 with the desired length. The third peg 640 may then be inserted through the third drill hole 410 and into the third cavity 642, as shown in FIG. 48. The insertion of the third peg 640 adds additional stability to the compression of the bones 262, 564.

The drill sleeve 590 may also be inserted into the fourth drill hole 412, as illustrated in FIG. 46. A drill may then be inserted into the opening 596 in the drill sleeve 590 to drill a fourth cavity 662 into the first bone 262. The fourth cavity 662 may pass through the fourth opening 514 in the nail 500. After the fourth cavity 662 is drilled a depth gauge may be inserted into the fourth cavity 662 through the drill sleeve 590 to measure the depth of the fourth cavity 662. Then the depth gauge and the drill sleeve 590 may be removed. Using the measured depth, the surgeon may select a fourth peg 660 with the desire length. The fourth peg 660 may then be inserted through the fourth drill opening 412 and into the fourth cavity 662, as illustrated in FIG. 48. The insertion of the fourth peg 660 may provide additional stability to the compression of the first bone 262 and the third bone 564.

Figure 53:
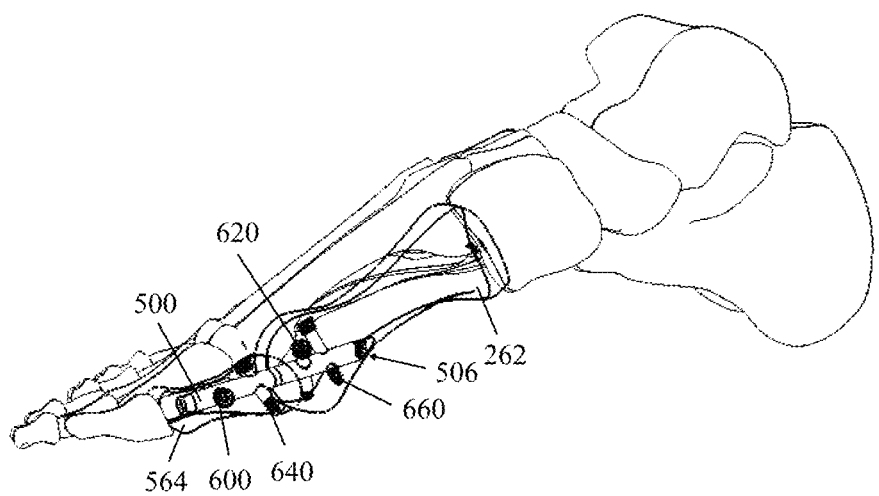
FIG. 53 is an isometric side view of the embodiment of FIG. 48 with the fixation guide of FIG. 33 removed from the patient's foot, in accordance with an aspect of the present invention.
Figure 54:
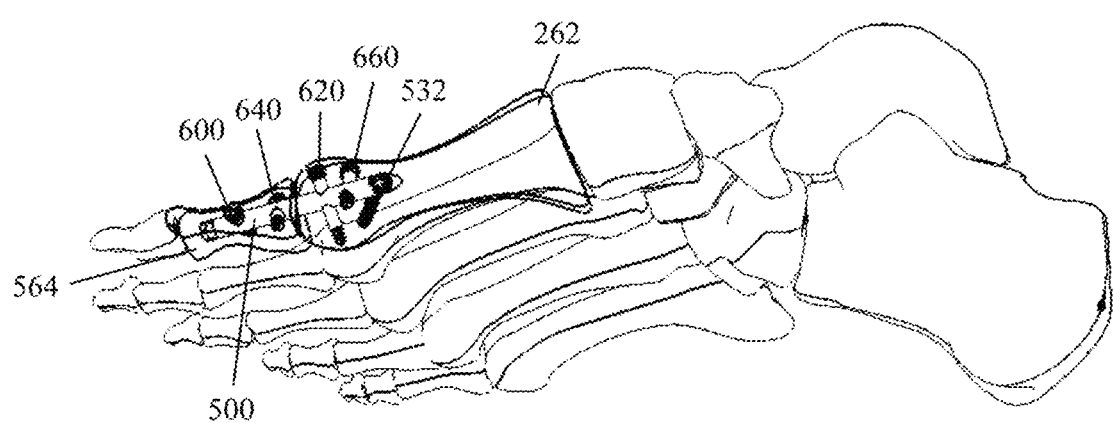
FIG. 54 is an isometric side view of the embodiment of FIG. 53 showing the locking screw inserted into the intramedullary nail of FIG. 39, in accordance with an aspect of the present invention.

Referring now to FIGS. 53 and 54, once at least the first and second peg 600, 620, although all four pegs 600, 620, 640, and 660 are shown in the depicted embodiment, are inserted into the first and third bones 262, 564, respectively, nail 500 may be detached from the outrigger assembly 402 and the fixation guide device 400 may be removed from the patient's foot, in step 372. Next, in step 374, a threaded locking drill guide may be threaded or not threaded for inserting the locking screw 532 into the first bone 262 through the engagement opening 518 of the intramedullary nail 500. Once the locking drill guide is secured, a cavity 680 for the locking screw 532 may be drilled through the engagement opening 518 and the depth measured, as described above with reference to drilling cavity 350 which will not be described again for brevity sake. Using the measured depth, the surgeon may select a locking screw 532 and insert the screw 532 into the cavity 680 to secure the nail 500 in position in the first bone 262 and the third bone 564. After the locking screw 532 is inserted the position and stability of the nail 500 may be verified using fluoroscopy. Once the position of the nail 500 is verified, a cap may be inserted into the fastening end 506 to prevent bone ingrowth or overgrowth in order to maintain the ability to remove nail 500 if necessary or desired. The cap may also include securing means to secure the cap to the nail 500 to prevent disengagement of the cap. Then, in step 376, the incision over the joint 560 may be closed by the surgeon.

Alternative intramedullary nails, for example, nail 700, as shown in FIGS. 56-59, may be used to replace intramedullary nails 200 and 500. The nail 700 may include a body 702, a closed end 704, a compression end or fastening end 706, and four openings 708, 710, 712, and 714. The four openings 708, 710, 712, and 714 may be disposed on independent planes and angularly spaced apart relative to each other. The amount of longitudinal and rotational movement of the nail 700 is limited by placing the four openings 708, 710, 712, and 714 at opposing angles oblique to the longitudinal axis of the nail 700. It is also contemplated that the intramedullary nail 700 may include any number of openings 708, 710, 712, 714 as may be necessary to secure the nail to a patient's bones with limited or no rotational or longitudinal movement after implantation. The second opening 710 may be an elongated opening to enable compression of a joint 732 which is medial the first opening 708 and the second opening 710 and configured to receive fastener 726. While the first opening 708, third opening 712, and fourth opening 714 may be configured to receive fasteners 724, 728, 730, respectively, and prevent movement along the longitudinal axis of the body 702. Alternative fasteners may also be used with the intramedullary nail 700, for example, fasteners or pegs 300, as shown in FIG. 21, and 600, 620, 640, 660, as shown in FIGS. 49-52. The compression end 706 includes a cam opening or insertion opening 716, which may be threaded, and a cam or cam member 718 for insertion into the cam opening 716. The cam 718 may include exterior threads 720 for engaging the threads of the cam opening 716 and a drive opening 722.

Figure 57:
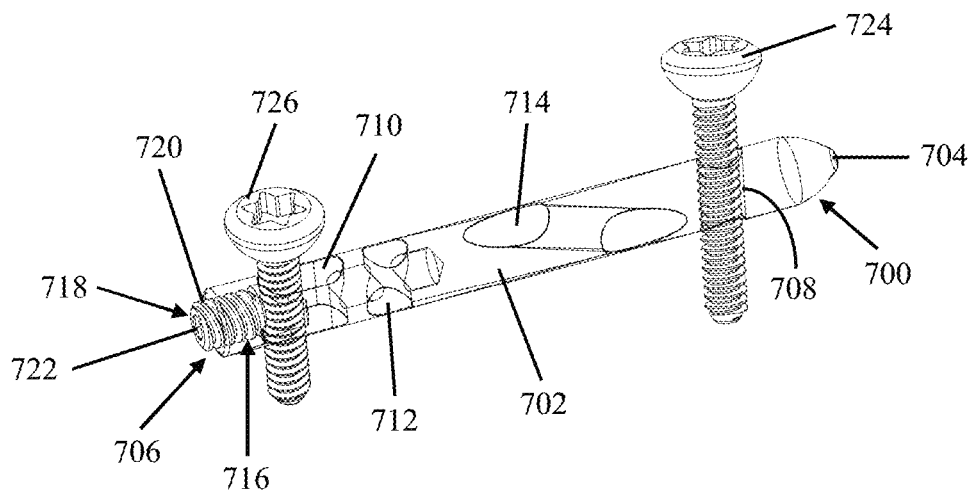
FIG. 57 is an isometric view of the intramedullary nail implant of FIG. 56 wherein the implant is transparent showing the openings and the compression cam, in accordance with an aspect of the present invention.
Figure 58:
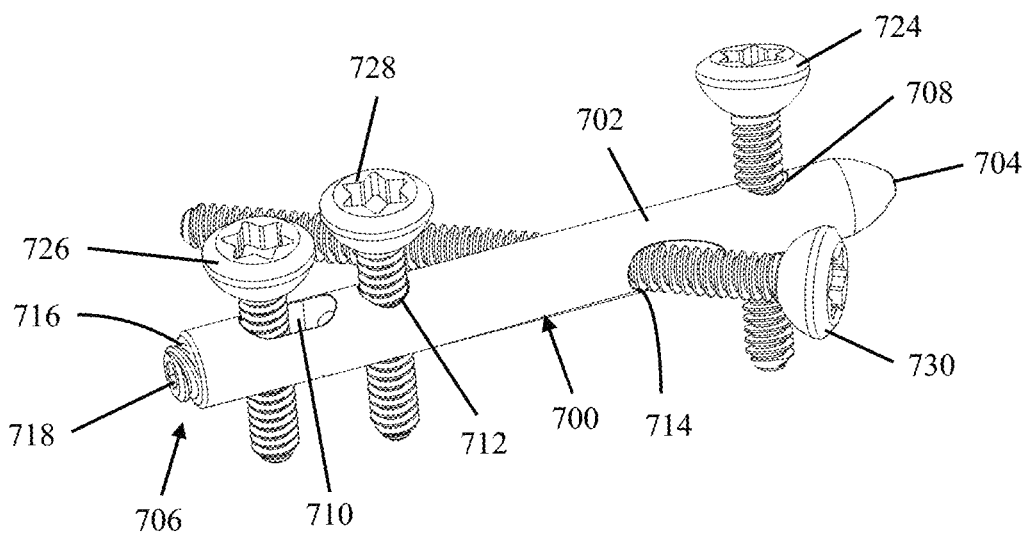
FIG. 58 is an isometric view of the intramedullary nail implant of FIG. 56 with four fasteners inserted into the nail implant, in accordance with an aspect of the present invention.
Figure 59:
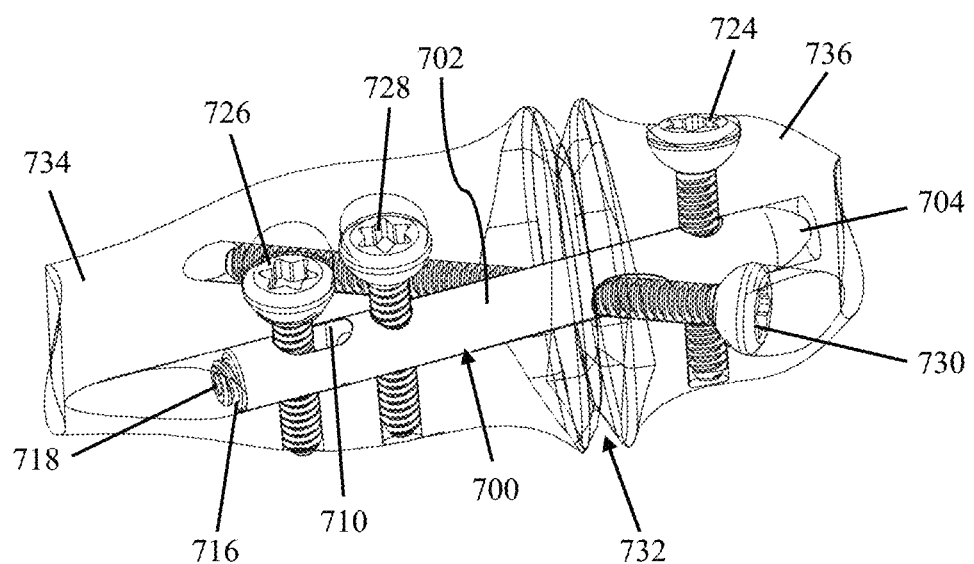
FIG. 59 is an isometric view of the intramedullary nail implant of FIG. 56 implanted into a patient's bones, in accordance with an aspect of the present invention.

The intramedullary nail 700 may be used during surgery to compress a joint 732, which may be, for example, joints 260, 560 described in greater detail above. The nail 700 may be inserted into a patient in place of nails 200 and 500. Once inserted into a cavity within the patient's bones 734, 736 which passes through a patient's joint 732, the surgeon may insert a first fastener 724 into the first opening 708 and into the second bone 736. Next a second fastener 726 may be inserted into the first bone 734 through the second or elongated opening 710 at a position within the opening 710 closest to the compression end 706. Then a screw driver, not shown, may be inserted to engage the drive opening 722 of the cam 718 and turned to advance the cam 718 along the cam opening 716. As the cam 718 is advanced along the cam opening 716 into the body 702 of the nail 700, the cam 718 engages the shaft of the second fastener 726, as shown in FIG. 57, and pushes the second fastener 726 along the elongated opening 710 to compress the first bone 734 and second bone 736 of the joint 732. Once the desired compression is achieved, a third fastener 728 may be inserted into the first bone 734 through the third opening 712 to secure the joint 732 in compression. A fourth fastener 730 may be inserted into the second bone 736 through the fourth opening 714 to secure the joint 732 in compression.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. A method for using an intramedullary nail for fixation of two bone pieces, comprising:
   preparing the two bone pieces for fixation;
   drilling over a guidewire to create a cavity for the intramedullary nail in at least one of the two bone pieces;
   obtaining a fixation guide device;
   inserting the intramedullary nail into the cavity;
   engaging a portion of the fixation guide device to the intramedullary nail;
   inserting a first guidewire through a first drill sleeve of the fixation guide device and into a distal bone piece of the two bone pieces;
   inserting a second drill sleeve into a first drill hole of the fixation guide device;
   inserting a second guidewire through the second drill sleeve and into the two bone pieces;
   disengaging the intramedullary nail and the fixation guide device;
   inserting a first fastener into the distal bone piece and the intramedullary nail; and
   inserting a second fastener through the two bone pieces and the intramedullary nail.

2. The method of claim 1, wherein the intramedullary nail includes a securing screw hole at a first end of the intramedullary nail and at least one peg hole.

3. The method of claim 1, wherein the fixation guide device includes a frame with at least two drill holes and a compression device.

4. The method of claim 1, further comprising drilling a first opening over the first guidewire that aligns with a first peg hole in the intramedullary nail.

5. The method of claim 4, further comprising inserting a first peg into the first opening in the distal bone piece and through the first peg hole.

6. The method of claim 5, further comprising using the first peg and compression device to compress the two bone pieces.

7. The method of claim 4, further comprising drilling a second opening over the second guidewire that mates with a second peg hole in the intramedullary nail.

8. The method of claim 7, further comprising inserting a second peg into a second opening in the two bone pieces and through a second peg hole to secure the two bone pieces.

9. The method of claim 1, further comprising:
inserting the second drill sleeve into a second drill hole of the fixation guide device and drilling a third opening that aligns with a third peg hole;
inserting a third peg into the third opening and through the third peg hole to secure the two bone pieces; and
verifying stability and position using fluoroscopy.

10. The method of claim 9, further comprising:
inserting the second drill sleeve into a third drill hole of the fixation guide device and drilling a fourth opening that aligns with a fourth peg hole;
inserting a fourth peg into the fourth opening and through the fourth peg hole to secure the two bone pieces; and
verifying stability and position using fluoroscopy.

11. A method of inserting an intramedullary nail into two bones for fixation of the two bones, comprising:
preparing the two bones for fixation;
securing an alignment guide to the two bones to position a guidewire across the two bones;
drilling over the guidewire to create a cavity for the intramedullary nail that passes through the two bones;
obtaining a fixation guide device;
attaching the intramedullary nail to a compression device of the fixation guide device, the intramedullary nail having a body with a first end and a second end, and further comprising:
a fastening end at the first end of the body, the fastening end comprising:
a first fastening segment extending away from the first end of the body a first distance along a longitudinal axis;
a second fastening segment extending away from the first end of the body a second distance along the longitudinal axis;
an insertion opening extending from the first end into the body along the longitudinal axis of the body; and
an engagement opening extending from the first end through the body to an exterior surface;
at least two openings positioned oblique to the longitudinal axis of the body between the first end and the second end of the body, wherein the at least two openings comprise:
three first openings; and
a second elongated opening, wherein the insertion opening of the fastening end engages the second elongated opening;
inserting the intramedullary nail into the cavity;
inserting a drill sleeve into a drill hole at a second end of the fixation guide device;
detaching the intramedullary nail from the fixation guide device and removing the fixation guide device; and
inserting a locking screw into a securing screw hole.

12. The method of claim 11, wherein the first distance along the longitudinal axis is greater than the second distance along the longitudinal axis.

13. The method of claim 12, wherein the first fastening segment is offset from the second fastening segment along the longitudinal axis.

14. The method of claim 13, wherein a portion of the engagement opening overlaps with a portion of the insertion opening to form an oblique opening at the first end of the body that extends between the first fastening segment and the second fastening segment.

15. The method of claim 14, wherein the oblique opening intersects and overlaps the longitudinal axis at the first end.

16. The method of claim 15, wherein the intramedullary nail further comprises a closed end at the second end of the body.

17. The method of claim 11, further comprising inserting the drill sleeve into a second drill hole at a first end of the fixation guide device.

18. A method of inserting an intramedullary nail into two bones for fixation of the two bones, comprising:
preparing the two bones for fixation;
securing an alignment guide to the two bones to position a guidewire across the two bones;
drilling over the guidewire to create a cavity for the intramedullary nail that passes through the two bones;
obtaining a fixation guide device, the fixation guide device comprising:
a frame having a first end and a second end, the frame further comprising:
at least one drill hole; and
a first arm;
a compression device removably coupled to the first end of the frame and comprising:
a compression member;
a bolt; and
a knob, wherein bolt rotatably engages the compression member at the first end and is secured to the knob at the second end, and the bolt extends through and rotatably couples to a first opening in the first arm of the frame;
attaching the intramedullary nail to the compression device of the fixation guide device;
inserting the intramedullary nail into the cavity;
inserting a drill sleeve into a first drill hole at a second end of the fixation guide device;
inserting the drill sleeve into a second drill hole at a first end of the fixation guide device;
detaching the intramedullary nail from the fixation guide device and removing the fixation guide device; and
inserting a locking screw into a securing screw hole.

\* \* \* \* \*